US009232980B2

(12) United States Patent
Kishi

(10) Patent No.: US 9,232,980 B2
(45) Date of Patent: Jan. 12, 2016

(54) OPERATION INPUT DEVICE AND METHOD OF INITIALIZING OPERATION INPUT DEVICE

(71) Applicant: OLYMPUS CORPORATION, Tokyo (JP)

(72) Inventor: Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/253,925

(22) Filed: Apr. 16, 2014

(65) Prior Publication Data

US 2014/0229007 A1 Aug. 14, 2014

Related U.S. Application Data

(63) Continuation of application No. PCT/JP2012/077381, filed on Oct. 17, 2012.

(30) Foreign Application Priority Data

Oct. 18, 2011 (JP) ................................. 2011-228677

(51) Int. Cl.
*A61B 19/00* (2006.01)
*A61B 6/00* (2006.01)
(Continued)

(52) U.S. Cl.
CPC ............... *A61B 19/2203* (2013.01); *B25J 3/00* (2013.01); *B25J 13/02* (2013.01); *G05G 9/04737* (2013.01); *G06F 3/0346* (2013.01); *A61B 2019/2223* (2013.01); *A61B 2019/2269* (2013.01)

(58) Field of Classification Search
USPC .......... 700/245, 257, 250; 901/14, 15, 46, 30; 345/650; 600/424
See application file for complete search history.

(56) References Cited

U.S. PATENT DOCUMENTS 5,343,391 A * 8/1994 Mushabac .......... A61C 13/0004
433/72
5,596,683 A 1/1997 Kasagami et al.
(Continued)

FOREIGN PATENT DOCUMENTS

JP H06-198584 A 7/1994
JP H08-276390 A 10/1996
(Continued)

OTHER PUBLICATIONS

International Search Report dated Jan. 29, 2013 issued in PCT/JP2012/077381.
(Continued)

*Primary Examiner* — Ronnie Mancho
(74) *Attorney, Agent, or Firm* — Scully, Scott, Murphy & Presser, P.C.

(57) ABSTRACT

An operation input device that has multi jointed arms includes: a holding unit that holds proximal ends of the multi-jointed arms in a state in which a relative positional relationship between the proximal ends is fixed; a detection unit that detects a joint movement amount that represents a movement of a joint by a rotation angle or a translational displacement from an unknown initial joint value; engagement units that are provided in distal ends of the multi jointed arms; a data acquisition unit that acquires a plurality of sets of joint movement amounts detected by the detection unit in a time series when engaging and moving the distal ends; and an initial value calculation unit that calculates the unknown initial joint value under a condition that a relative positional relationship between the distal ends is fixed via the engagement units.

10 Claims, 14 Drawing Sheets

(51) Int. Cl.
*G06T 3/60* (2006.01)
*B25J 13/02* (2006.01)
*G06F 3/0346* (2013.01)
*G05G 9/047* (2006.01)
*B25J 3/00* (2006.01)

(56) References Cited

U.S. PATENT DOCUMENTS

| | | | | |
|---|---|---|---|---|
| 6,309,397 | B1* | 10/2001 | Julian et al. | 606/130 |
| 6,468,265 | B1* | 10/2002 | Evans | A61B 19/22 600/103 |
| 6,661,571 | B1* | 12/2003 | Shioda et al. | 359/372 |
| 6,949,106 | B2* | 9/2005 | Brock | A61B 17/0469 606/130 |
| 6,965,812 | B2* | 11/2005 | Wang et al. | 700/258 |
| 8,062,288 | B2* | 11/2011 | Cooper | A61B 19/2203 600/102 |
| 8,504,201 | B2* | 8/2013 | Moll | A61B 19/2203 700/1 |
| 9,060,678 | B2* | 6/2015 | Larkin | A61B 1/00087 1/1 |
| 2002/0133173 | A1 | 9/2002 | Brock et al. | |
| 2003/0151379 | A1 | 8/2003 | Gosselin et al. | |
| 2005/0043718 | A1* | 2/2005 | Madhani | A61B 19/22 606/1 |
| 2008/0046122 | A1* | 2/2008 | Manzo | A61B 1/00149 700/245 |
| 2008/0177285 | A1* | 7/2008 | Brock et al. | 606/130 |
| 2008/0180392 | A1 | 7/2008 | Kishi et al. | |
| 2011/0130761 | A1* | 6/2011 | Plaskos | A61B 17/155 606/87 |
| 2012/0071752 | A1* | 3/2012 | Sewell et al. | 600/424 |
| 2013/0041292 | A1* | 2/2013 | Cunningham | 601/2 |
| 2013/0345718 | A1* | 12/2013 | Crawford | A61B 17/025 606/130 |
| 2014/0039681 | A1* | 2/2014 | Bowling | A61B 19/2203 700/261 |
| 2014/0229007 | A1* | 8/2014 | Kishi | A61B 19/2203 700/257 |

FOREIGN PATENT DOCUMENTS

| | | |
|---|---|---|
| JP | H08-323665 A | 12/1996 |
| JP | 09-011168 A | 1/1997 |
| JP | 2003-181782 A | 7/2003 |
| JP | 2006-286016 A | 10/2006 |
| JP | 2007-510232 A | 4/2007 |
| JP | 2008-173724 A | 7/2008 |
| JP | 2010-524548 A | 7/2010 |
| WO | WO 2005/043365 A2 | 5/2005 |
| WO | WO 2009/034477 A2 | 3/2009 |
| WO | 2010/091722 A1 | 8/2010 |
| WO | WO 2011/058893 A1 | 5/2011 |

OTHER PUBLICATIONS

Extended Supplementary European Search Report dated Jun. 26, 2015 from related European Application No. 12 84 1444.8.

Park, C., et al., "Dual Arm Robot Manipulator and Its Easy Teaching System", Proceedings of 2009 IEEE International Symposium on Assembly and Manufacturing, Nov. 17-20, 2009, ISAM 2009, pp. 242-247.

Japanese Office Action dated Sep. 29, 2015 from related Japanese Patent Application No. 2011-228677, together with an English language translation.

* cited by examiner

OPERATION INPUT DEVICE AND METHOD OF INITIALIZING OPERATION INPUT DEVICE

This application is a continuation application based on a PCT Patent Application No. PCT/JP2012/077381, filed Oct. 17, 2012, whose priority is claimed on Japanese Patent Application No. 2011-228677 filed Oct. 18, 2011. The contents of both the PCT Application and the Japanese Application are incorporated herein by reference.

BACKGROUND OF THE INVENTION

1. Field of the Invention

The present invention relates to an operation input device and a method of initializing the operation input device. The present invention relates to, for example, an operation input device that has a plurality of multi-jointed arms and performs an operation input by moving the plurality of multi-jointed arms, and a method of initializing the operation input device.

2. Description of Related Art

In the related art, in an apparatus (for example, a remote control robot, an operation input device for performing a surgical assistant of a surgical operation or the like) in which an actuating unit is held in a plurality of multi-jointed robots, there has been known a configuration that uses an operation input device including an multi-jointed arm having the same degree of freedom as that of the actuating unit, when performing the movement operation of the actuating unit. For example, in a medical manipulator system of a master-slave type, a master manipulator, which inputs the movement of the slave manipulator, constitutes such an operation input device.

Such the operation input device detects a rotation angle of the joint detected by each joint of the multi-jointed arm, the length of the arm between the joints or the like, and detects the position and the orientation of an operation unit provided on the multi-jointed arm corresponding to the actuating unit and transmits the detected data to a control device of the multi-jointed robot. The control device of the multi-jointed robot performs the control of driving the actuating unit in accordance with the position and the orientation that is transmitted from the operation input device.

The joint of the multi-jointed arm of the operation input device is equipped with a sensor that detects a rotation angle of the joint and a translation amount of the arm between the adjacent joints. However, in order to promote a low cost, in many cases, an encoder which cannot detect an absolute value is used.

In such an operation input device, in an initial state, a relationship between an output value of the encoder and the angle or the length of the joint is indefinite. For this reason, in order to perform the accurate operation input, there is a need for the initialization that performs an identification task between the output value of the encoder and the value of a physical joint angle or joint length.

For example, Published Japanese Translation No. 2007-510232 of the PCT International Publication discloses a force reflecting haptic interface that includes a docking station fixed to a base, and a rod-like user interface having a distal end capable of being held in a cylinder portion provided in the docking station.

In the force reflecting haptic interface, it is possible to set (initialize) a rest point and a home position of the distal end to a zero position or a user-designated home position, by holding the distal end of the user interface in the cylinder portion of the docking station of the fixed position.

SUMMARY OF THE INVENTION

According to a first aspect of the present invention, an operation input device that has two or more multi-jointed arms which have a plurality of joints in series having a degree of freedom of rotation or translation and are configured so that a position and an orientation of a distal end thereof relative to a proximal end thereof are changed, includes: a holding unit that holds the proximal ends of the multi-jointed arms in a state in which a relative positional relationship between the proximal ends is fixed; a detection unit that is provided in each of the plurality of joints to detect a joint movement amount that represents a movement of each of the plurality of joints by a rotation angle or a translational displacement from an unknown initial joint value; an engagement unit that is provided in each of the distal ends of the multi jointed arms and is engaged so that a relative position between the distal ends is fixed; a data acquisition unit that acquires a plurality of sets of joint movement amounts detected by the detection unit in a time series when engaging the distal ends of the multi-jointed arms via the engagement unit and moving the mutually engaged distal ends; and an initial value calculation unit that calculates the unknown initial joint value under a condition that a relative positional relationship between the distal ends is fixed via the engagement unit based on the plurality of sets of joint movement amounts acquired by the data acquisition unit in a time series.

According to a second aspect of the present invention, in the operation input device according to the first aspect, the initial value calculation unit may be configured to generate a simultaneous equation that sets the initial value of the joint movement amount as an unknown number based on a kinematical relational expression that describes positions and orientations of the distal ends of the multi-jointed arms, and the plurality of sets of joint movement amounts acquired by the data acquisition unit in a time series. The initial value calculation unit may be configured to solve the simultaneous equation to calculate the initial value of the joint movement amount.

According to a third aspect of the present invention, in the operation input device according to the second aspect, the initial value calculation unit may be configured to solve the simultaneous equation by performing a convergent calculation until a residual error expression to be zero in the simultaneous equation is less than or equal to a convergent determination value.

According to a fourth aspect of the present invention, in the operation input device according to the third aspect, the initial value calculation unit may be configured to perform a warning when the convergent calculation is not finished within a predetermined time.

According to a fifth aspect of the present invention, in the operation input device according to the fourth aspect, the warning may include warning of a breakdown of the detection unit.

According to a sixth aspect of the present invention, in the operation input device according to any one of the first aspect to the fifth aspect, the engagement unit may directly engage the distal ends of the multi-jointed arms and fix the relative position between the distal ends.

According to a seventh aspect of the present invention, in the operation input device according to any one of the first aspect to fifth aspect, the engagement unit may engage the distal ends of the multi-jointed arms so as to be spherically rotatable about one point.

According to an eighth aspect of the present invention, in the operation input device according to any one of the first aspect to fifth aspect, the engagement unit may be engaged with an engagement unit of one of the multi-jointed arms to be an engagement target via an intermediate member that constantly maintains a distance between the engagement unit and the engagement unit of the multi-jointed arms to be the engagement target.

According to a ninth aspect of the present invention, in the operation input device according to any one of the first aspect to fifth aspect, the engagement unit may be engaged by fixing a relative position and a relative orientation between the distal ends of the multi-jointed arms.

According to a tenth aspect of the present invention, a method of initializing an operation input device that has two or more multi-jointed arms which have a plurality of joints in series having a degree of freedom of rotation or translation and are configured so that a position and an orientation of a distal end thereof relative to a proximal end thereof are changed, and a detection unit which is provided in each of the plurality of joints to detect a joint movement amount that represents a movement of each of the plurality of joints by a rotation angle or a translational displacement from an unknown initial joint value, includes: a holding process of holding the proximal ends of the multi-jointed arms in a state in which a relative positional relationship between the proximal ends is fixed; an engaging process of engaging the distal ends of the multi-jointed arms are engaged so that a relative position between the distal ends is fixed; a data acquisition process of acquiring a plurality of sets of joint movement amounts in a time series from the detection unit that is provided in each of the plurality of joints of the mutually engaged multi-jointed arms while moving the distal ends of the mutually engaged multi-jointed arms; and an initial value calculation process of calculating the unknown initial joint value under a condition that a relative positional relationship between the distal ends is fixed by an engagement based on the plurality of sets of joint movement amounts acquired in the data acquisition process in a time series.

DETAILED DESCRIPTION OF THE INVENTION

Figure 1A:
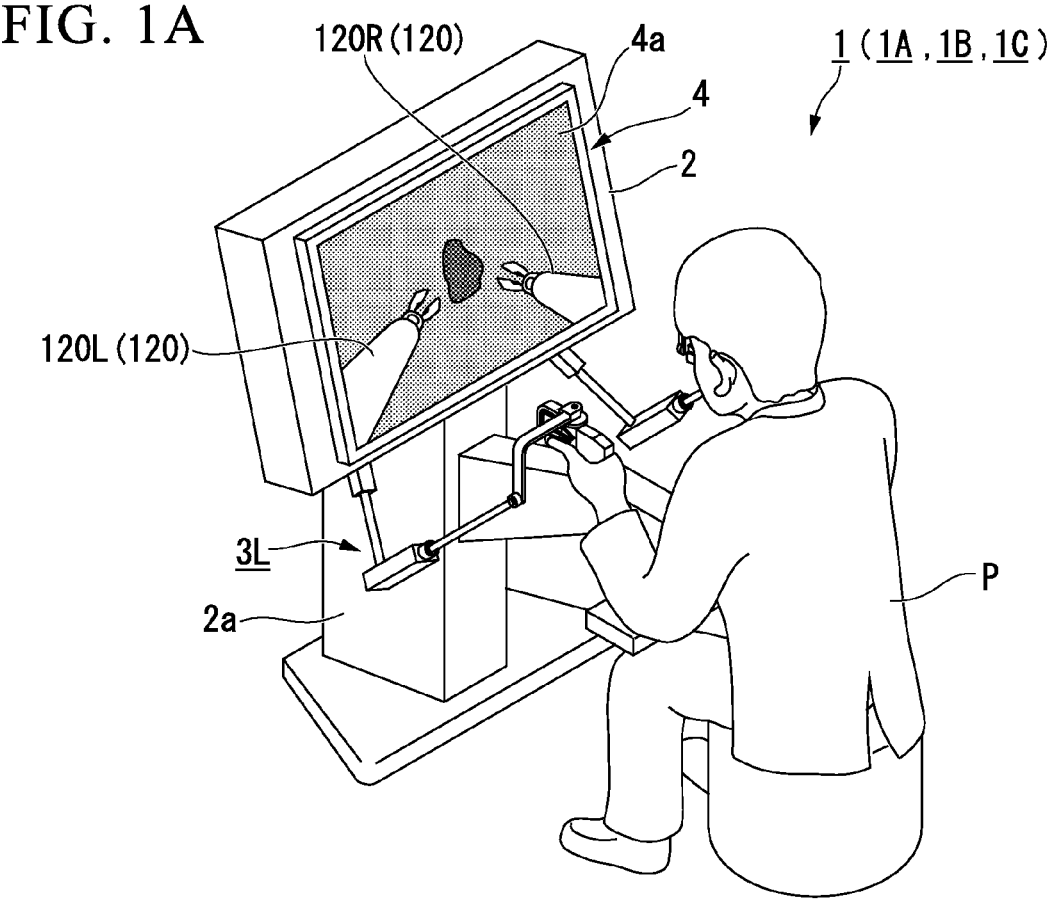
FIG. 1A is a schematic perspective view that illustrates an example of an operation input device according to a first embodiment of the present invention.

Hereinafter, embodiments of the present invention will be described with reference to the accompanying drawings. In the drawings, even in the case of other embodiments, the same or equivalent members are denoted by the same reference numerals, and descriptions thereof will be omitted here.

First Embodiment

An operation input device according to a first embodiment of the present invention will be described.

Figure 1B:
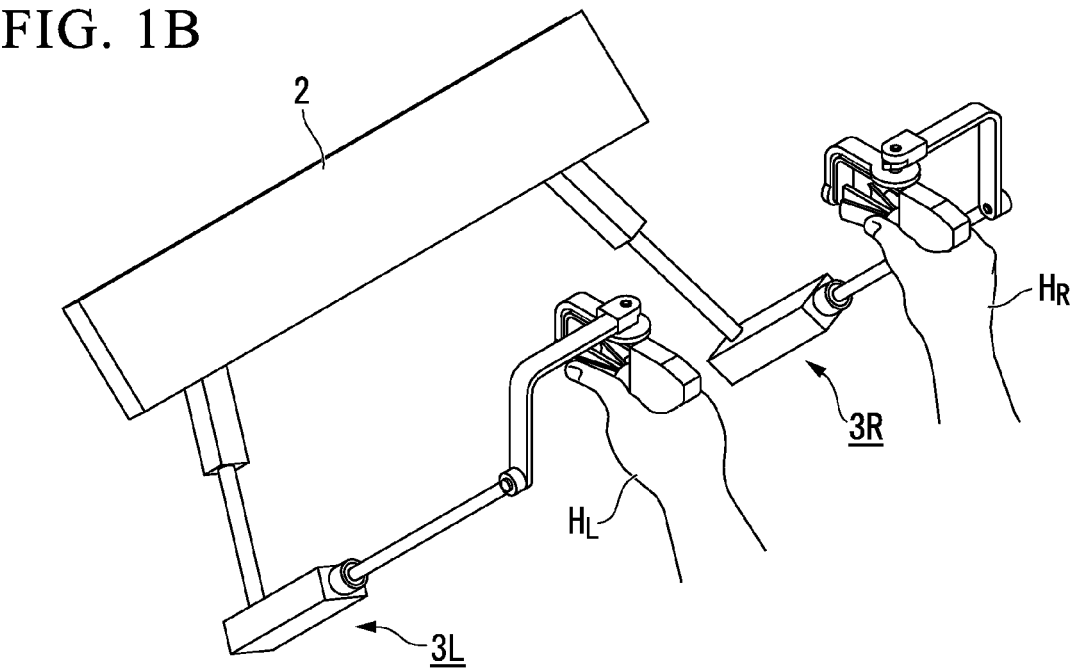
FIG. 1B is a perspective view of main parts of the operation input device according to the first embodiment of the present invention.

FIG. 1A is a schematic perspective view that illustrates an example of the operation input device according to the first embodiment of the present invention. FIG. 1B is a perspective view of main parts of the operation input device according to the first embodiment of the present invention.

Figure 2A:
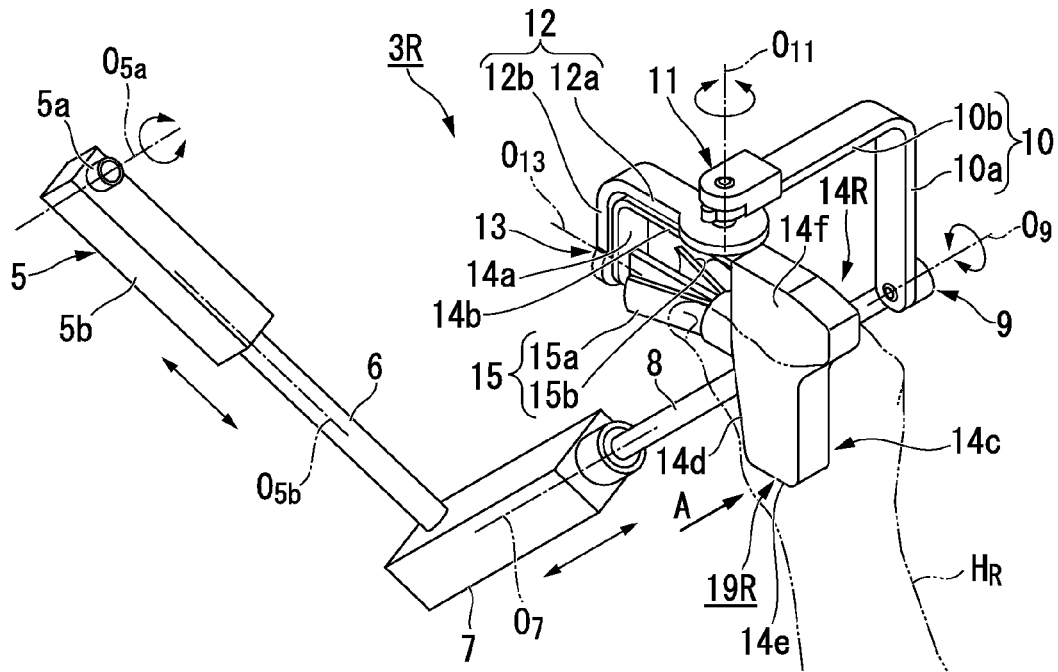
FIG. 2A is a schematic perspective view that illustrates a configuration of a multi-jointed arm of the operation input device according to the first embodiment of the present invention.
Figure 2B:
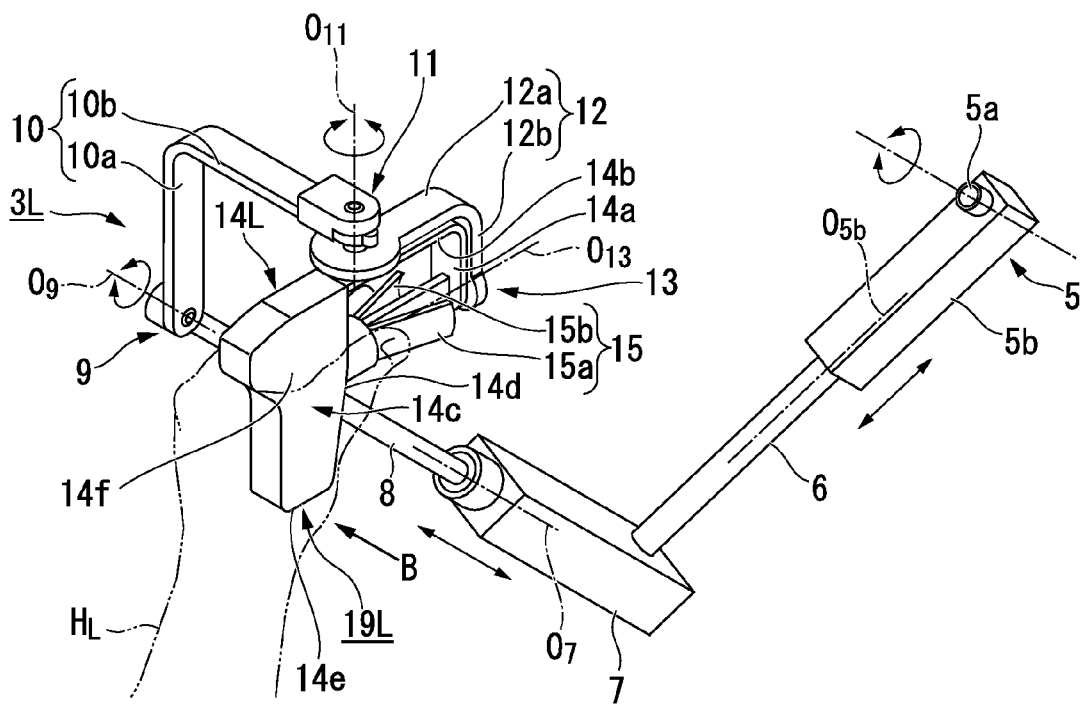
FIG. 2B is a schematic perspective view that illustrates a configuration of a multi-jointed arm of the operation input device according to the first embodiment of the present invention.
Figure 3A:
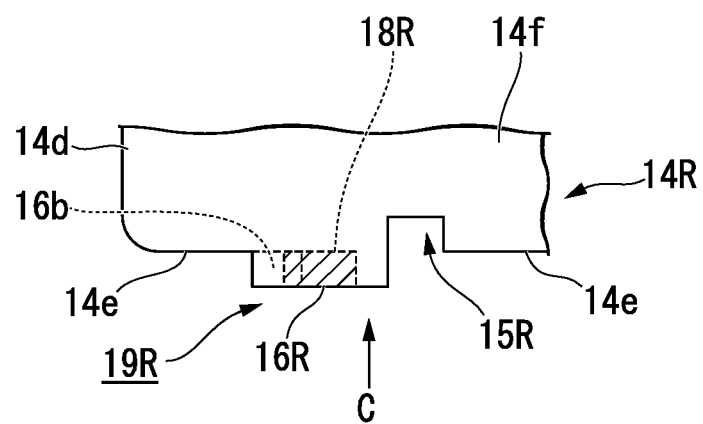
FIG. 3A is a view in a direction of an arrow A in FIG. 2A.
Figure 3B:
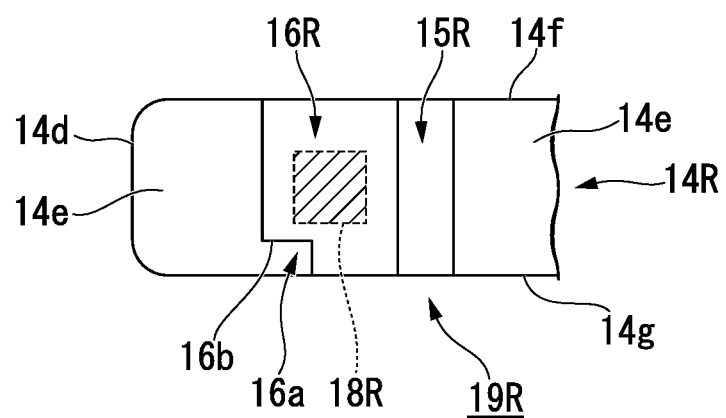
FIG. 3B is a view in a direction of an arrow C in FIG. 3A.
Figure 4A:
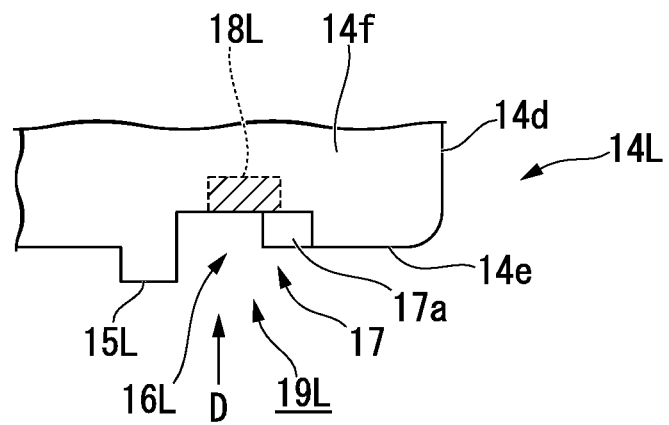
FIG. 4A is a view in a direction of an arrow B in FIG. 2B.
Figure 4B:
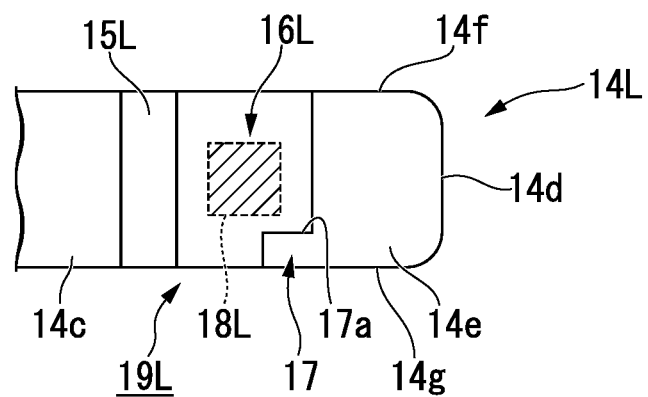
FIG. 4B is a view in a direction of an arrow D in FIG. 4A.
Figure 5A:
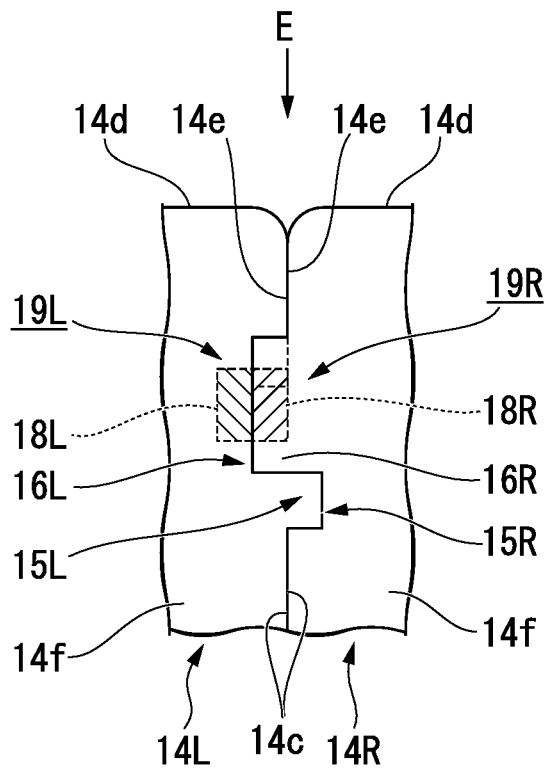
FIG. 5A is a schematic plan view that illustrates a state in which engagement units of the operation input device according to the first embodiment of the present invention are engaged with each other.
Figure 5B:
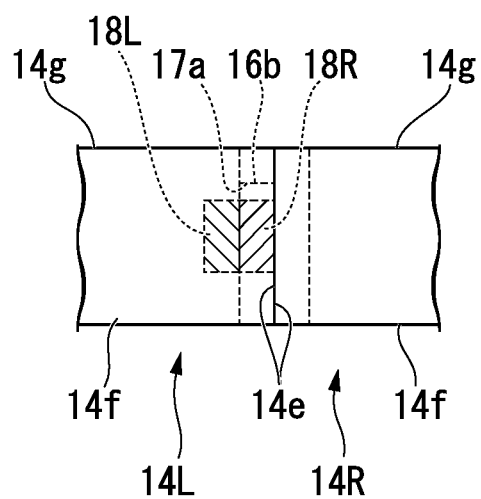
FIG. 5B is a view in a direction of an arrow E in FIG. 5A.
Figure 6:
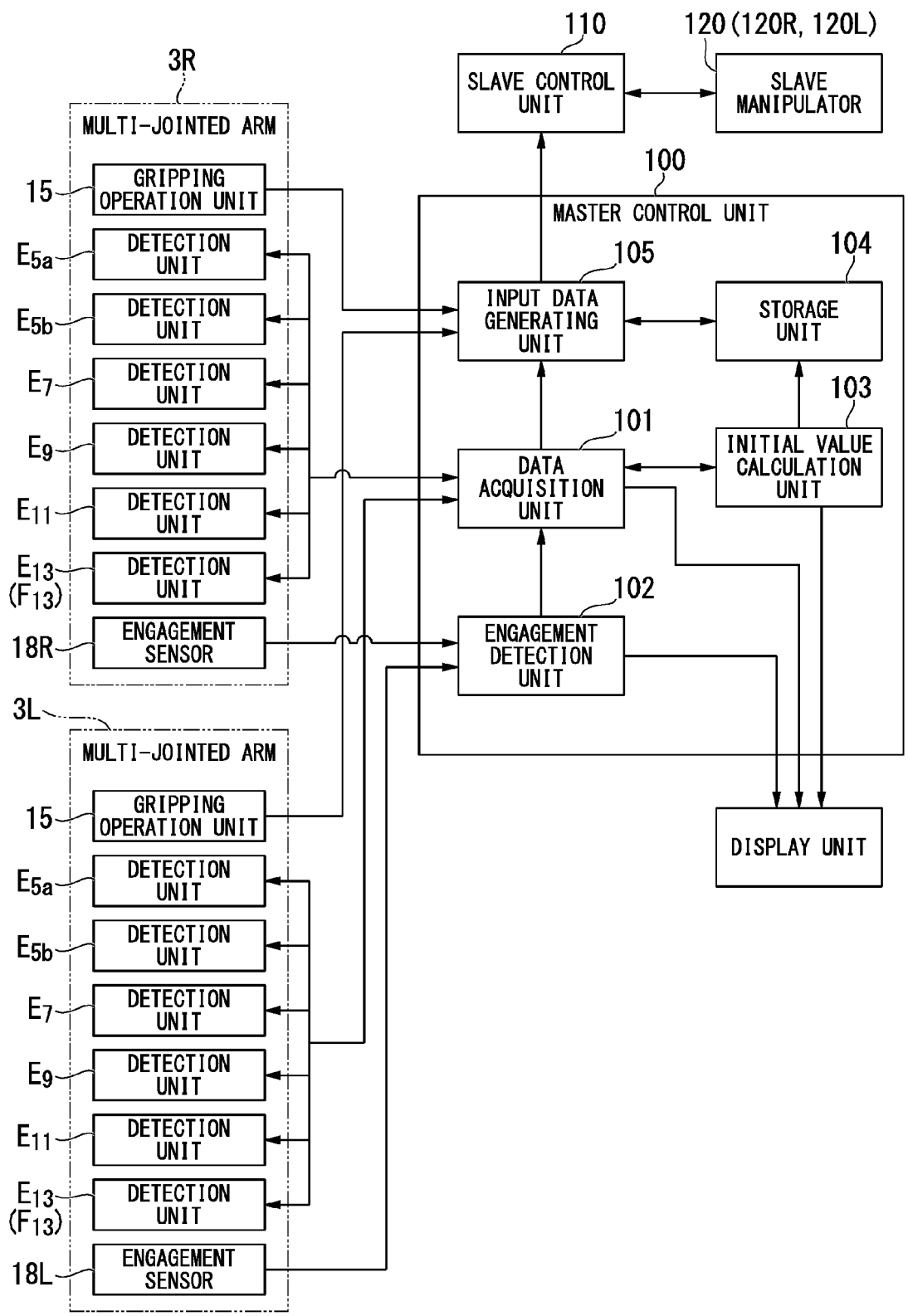
FIG. 6 is a functional block diagram that illustrates a functional configuration of a control means of the operation input device according to the first embodiment of the present invention.

FIGS. 2A and 2B are schematic perspective views that illustrate a configuration of a multi-jointed arm of the operation input device according to the first embodiment of the present invention. FIG. 3A is a view in a direction of an arrow A in FIG. 2A. FIG. 3B is a view in a direction of an arrow C in FIG. 3A. FIG. 4A is a view in a direction of an arrow B in FIG. 2B. FIG. 4B is a view in a direction of an arrow D in FIG. 4A. FIG. 5A is a schematic plan view that illustrates a state in which engagement units of the operation input device according to the first embodiment of the present invention are engaged with each other. FIG. 5B is a view in a direction of an arrow E in FIG. 5A. FIG. 6 is a functional block diagram that illustrates a functional configuration of a control means of the operation input device according to the first embodiment of the present invention.

As an example, a master manipulator 1 (operation input device) according to the present embodiment can be used as an operation input device that performs the operation of the slave manipulator in a master-slave type medical manipulator system. Herein, the master-slave type medical manipulator system is a system that has a master manipulator and a slave manipulator each including a multi-jointed arm, causes the multi-jointed arm of the slave manipulator to follow the movement of the multi-jointed arm of the master manipulator by moving the multi-jointed arm of the master manipulator, and remotely controls the slave manipulator.

As shown in FIGS. 1A and 1B, a schematic configuration of the master manipulator 1 includes a main body frame 2 (holding unit), a display unit 4, multi-jointed arms 3R and 3L (refer to FIG. 1B for the multi-jointed arm 3R), and a master control unit 100 (not shown in FIGS. 1A and 1B, see FIG. 6).

The main body frame 2 is a holding unit that holds the respective proximal ends of the multi-jointed arms 3R and 3L in a state in which a mutual relative positional relationship is fixed. In the present embodiment, the main body frame 2 has a substantially rectangular plate shape and is fixed in a horizontal direction on an upper end of a stand portion 2a provided on a bottom surface in a diagonally sloped manner.

Furthermore, in a center portion of the main body frame 2, a display unit 4 is provided which displays a captured image of the slave manipulator 120 using a camera (not shown) so that an operator P can monitor a state in which the slave manipulator 120 (see FIG. 6) is moved.

On a display screen 4a of the display unit 4 shown in FIG. 1A, an image of a slave manipulator 120R operated by the multi-jointed arm 3R and an image of a slave manipulator 120L operated by the multi-jointed arm 3L are displayed.

As a configuration of the display unit 4, for example, it is possible to adopt a configuration of a liquid crystal panel, a CRT monitor, or the like.

As shown in FIG. 1B, if a side in the main body frame 2 provided with the display unit 4 is a front side, a proximal end of the multi-jointed arm 3R is fixed to a right side of a lower end portion when viewed from the front side. A distal end of the multi-jointed arm 3R is located at the front side of the main body frame 2. Furthermore, a proximal end of the multi-jointed arm 3L is fixed to a left side of the lower end portion when viewed from the front side of the main body frame 2. A distal end of the multi-jointed arm 3L is located at the front side of the main body frame 2. For this reason, in the fixing positions of each proximal end of the multi-jointed arms 3R and 3L, the respective positional coordinates on the main body frame 2 are known and are horizontally separated from each other by a constant distance.

Due to such an arrangement, the operator P is able to operate the distal ends of the multi-jointed arms 3L and 3R while monitoring the movement of the slave manipulators 120L and 120R in the display screen 4a, for example, in the state of sitting on the front of the main body frame 2.

The plurality of multi-jointed arms 3R and 3L have a plurality of joints in series having a degree of freedom of the rotation or the translation and are configured so that the position and the orientation of the distal end to the proximal end can be changed. The number, configuration, and arrangement of the respective arms and joints can be suitably set depending on the need of operation input information of an operation target. However, in the present embodiment, the multi-jointed arm 3R is used for the operation input of a right hand, and the multi-jointed arm 3L is used for the operation input of a left hand.

In the present embodiment, an example of a case in which the slave manipulators 120R and 120L each include gripping forceps at the distal ends thereof and multi-jointed arms in which the degree of movement freedom of the gripping forceps is six degrees of freedom will be described.

For this reason, in the present embodiment, the multi-jointed arms 3R and 3L have substantially the same configuration except that the handles are different from each other in the distal ends.

As shown in FIG. 2A, a schematic configuration of the multi-jointed arm 3R includes a first joint 5 (joint), an arm 6, a second joint 7 (joint), an arm 8, a third joint 9 (joint), an L-shaped arm 10, a fourth joint 11 (joint), an L-shaped arm 12 (arm), a fifth joint 13 (joint), and a right hand operation arm 14R (arm) from the proximal end toward the distal end.

The first joint 5 is a joint with two degrees of freedom that includes a rotational joint 5a and a linear driving joint 5b. The rotational joint 5a has a degree of freedom in turn about a rotational axis $O_{5a}$ fixed to the main body frame 2 and extends in a direction intersecting the main body frame 2. The linear driving joint 5b has a degree of freedom in translation along a linear driving axis $O_{5b}$ which is an axis perpendicular to the rotational axis $O_{5a}$.

Furthermore, although it is not shown in FIG. 2A, the first joint 5 is provided with a detection unit $E_{5a}$ and a detection unit $E_{5b}$. The detection unit $E_{5a}$ detects a rotation angle that represents a rotational amount of the rotational joint 5a (see FIG. 6). The detection unit $E_{5b}$ detects the translational displacement that represents a translation amount of the linear driving joint 5b (see FIG. 6).

The detection units $E_{5a}$ and $E_{5b}$ are electrically connected to a master control unit 100, and are configured to be able to transmit the detection signals of the rotation angle and the translational displacement to the master control unit 100.

In the present embodiment, both of the detection units $E_{5a}$ and $E_{5b}$ adopt an increment type encoder. For this reason, when the electric conduction starts, or when the reset signal is transmitted from the master control unit 100 at the suitable timing, the rotation angle and the translational displacement can each be reset to zero. Thus, the detection signal of the detection unit $E_{5a}$ ($E_{5b}$) represents the rotation angle (displacement) based on the movement position of the joint when resetting the detection unit $E_{5a}$ ($E_{5b}$).

In the present embodiment, since it is difficult to know the values of joint coordinate systems that are set in the respective joints of the multi-jointed arms 3R and 3L at the time of reset, generally, the movement positions of the joints at the time of reset do not coincide with the values measured by the joint coordinate systems that are set in the respective joints in order to perform the kinematical calculation of the multi-jointed arms 3R and 3L.

Hereinafter, a value, in which the movement position of the joint at the time of reset is measured by the joint coordinate system, is referred to as an initial value of the movement of the joint.

The fixing position of the rotational joint 5a of the multi-jointed arm 3R with respect to the main body frame 2 defines a fixed position of the proximal end of the multi-jointed arm 3R.

The arm 6 is a rod-like member that is configured so as to be linearly movable by the linear driving joint 5b. The arm 6 is disposed coaxially with the linear driving axis $O_{5b}$. One end of the arm 6 is connected to the linear driving joint 5b. Furthermore, the other end of the arm 6 is fixed to the second joint 7.

Thus, when the linear driving joint 5b is linearly moved, the arm 6 advances or retreats along the linear driving axis $O_{5b}$, and the second joint 7 is translated together with the advance and the retreat of the arm 6.

The second joint 7 is a linear driving joint with one degree of freedom that has a degree of freedom of translation along the linear driving axis $O_7$. The linear driving axis $O_7$ is an axis that intersects the linear driving axis $O_{5b}$.

Furthermore, although it is not shown in FIG. 2A, the second joint 7 is provided with a detection unit $E_7$ (see FIG. 6) that detects the translational displacement representing the translation amount of the second joint 7.

The detection unit $E_7$ is electrically connected to the master control unit 100 and is configured so that it can transmit the detection signal of the translational displacement to the master control unit 100.

In the present embodiment, the detection unit $E_7$ adopts the same increment type encoder as the detection unit $E_{5b}$.

The arm 8 is a rod-like member that is configured so as to be linearly movable by the second joint 7. The arm 8 is disposed coaxially with the linear driving axis $O_7$. An end of the arm 8 is connected to the second joint 7. Furthermore, the other end of the arm 8 is fixed to the third joint 9.

Thus, when the second joint 7 is linearly moved, the arm 8 advances or retreats along the linear driving axis $O_7$, and the third joint 9 is translated together with the advance and the retreat of the arm 8.

The third joint 9 is a rotational joint with one degree of freedom that has a degree of freedom which turns about the rotational axis $O_9$. The rotational axis $O_9$ is an axis perpendicular to the linear driving axis $O_7$ and the rotational axis $O_{5a}$.

Furthermore, although it is not shown in FIG. 2A, the third joint 9 is provided with a detection unit $E_9$ (see FIG. 6) that detects the rotation angle representing the rotational amount of the third joint 9.

The detection unit $E_9$ is electrically connected to the master control unit 100 and is configured so that it can transmit the detection signal of the rotation angle to the master control unit 100.

In the present embodiment, the detection unit $E_9$ adopts the same increment type encoder as the detection unit $E_{5a}$.

The L-shaped arms 10 are an L-shaped arm member that is formed by a straight arm portion 10a and a straight arm portion 10b. One end of the straight arm portion 10a is connected to the third joint 9 and extends in a direction perpendicular to the rotational axis $O_9$. The straight arm portion 10b extends from the other end of the straight arm portion 10a in a direction along the rotational axis $O_9$.

In the present embodiment, the straight arm portion 10b extends from the straight arm portion 10a to a side provided with the multi-jointed arm 3L. A fourth joint 11 is connected to the distal end of the straight arm portion 10b.

Thus, when the third joint 9 turns, the L-shaped arm 10 turns about the rotational axis $O_9$, and the fourth joint 11 turns and moves along with the rotational movement of the L-shaped arm 10.

The fourth joint 11 is a rotational joint with one degree of freedom having a degree of freedom in turn about the rotational axis $O_{11}$. The rotational axis $O_{11}$ is an axis perpendicular to the straight arm portion 10b and the rotational axis $O_9$.

Furthermore, although it is not shown in FIG. 2A, the fourth joint 11 is provided with a detection unit $E_{11}$ (see FIG. 6) that detects the rotation angle representing the rotational amount of the fourth joint 11.

The detection unit $E_{11}$ is electrically connected to the master control unit 100 and is configured so that it can transmit the detection signal of the rotation angle to the master control unit 100.

In the present embodiment, the detection unit $E_{11}$ adopts the same increment type encoder as the detection unit $E_{5a}$.

The L-shaped arms 12 are an L-shaped arm member that is formed by a straight arm portion 12a and a straight arm portion 12b. One end of the straight arm portion 12a is connected to the fourth joint 11 and extends in a direction perpendicular to the rotational axis $O_{11}$. The straight arm portion 12b extends from the other end of the straight arm portion 12a in a direction along the rotational axis $O_{11}$.

Furthermore, the length of the straight arm portion 12a is shorter than that of the straight arm portion 10b of the L-shaped arm 10. Furthermore, a connection position of the straight arm portion 12a to the straight arm portion 10b (straight arm portion 10b of the L-shaped arm 10) is at the same direction side as an extension direction (direction perpendicular to the rotational axis $O_9$) of the straight arm portion 10a.

Furthermore, the extension direction of the straight arm portion 12b is the same direction as the extension direction of the straight arm portion 10a of the L-shaped arm 10, and a fifth joint 13 is connected to the distal end of the straight arm portion 12b in the extension direction.

Thus, the L-shaped arm 12 can be freely turned and moved about the rotational axis $O_{11}$ without interfering with the L-shaped arm 10. For this reason, the fifth joint 13 turns and moves along with the rotational movement of the L-shaped arm 12.

The fifth joint 13 is a joint with one degree of freedom having a degree of freedom in turn about the rotational axis $O_{13}$. The rotational axis $O_{13}$ is an axis perpendicular to the straight arm portion 12b and the rotational axis $O_{11}$. Furthermore, although it is not shown in FIG. 2A, the fifth joint 13 is provided with a detection unit $E_{13}$ (see FIG. 6) that detects the rotation angle representing the rotational amount of the fifth joint 13.

The detection unit $E_{13}$ is electrically connected to the master control unit 100 and is configured so that it can transmit the detection signal of the rotation angle to the master control unit 100.

In the present embodiment, the detection unit $E_{13}$ adopts the same increment type encoder as that of the detection unit $E_{5a}$.

The right hand operation arm 14R includes a straight arm portion 14a, a straight arm portion 14b, a grip unit 14c, and a gripping operation unit 15. One end of the straight arm portion 14a is connected to the fifth joint 13 and extends in a direction perpendicular to the rotational axis $O_{13}$. The straight arm portion 14b extends from the other end of the straight arm portion 14a in a direction along the rotational axis $O_{13}$, and in the same direction as the straight arm portion 12a of the L-shaped arm portion 12. The grip unit 14c extends from the end portion of the straight arm portion 14b opposite to which end portion the straight arm portion 14a is connected, in the same direction as the straight arm portion 14a. The gripping operation unit 15 is provided to protrude from the side surface 14d of the grip unit 14c facing the straight arm portion 14a to the straight arm portion 14a side.

In addition, when the first joint 5 side is defined as a proximal end of the multi-jointed arm 3R, the right hand operation arm 14R is defined as a distal end of the multi-jointed arm 3R.

The shape of the grip unit 14c can include a suitable three-dimensional shape that is easily gripped by the right hand $H_R$ from the side surface of the back side of the side surface 14d in which the straight arm portion 14b extends. In the present embodiment, the grip unit 14c is formed in a substantially plate shape that has substantially the same thickness as the widths of the straight arm portions 14a and 14b.

Hereinafter, in the side surface of the thickness direction adjacent to the side surface 14d, the side surface at which the thumb of the right hand $H_R$ is located when gripping the grip unit 14c is referred to as a side surface 14f. The side surface of the back side of the side surface 14f is referred to as a side surface 14g.

In the right hand operation arm 14R, the length of the straight arm portion 14a is shorter than that of the straight arm portion 12b of the L-shaped arm 12. Meanwhile, the straight arm portion 14a and the fifth joint 13 are connected to the straight arm portion 12b of the L-shaped arm 12 at the same direction side as the extension direction of the straight arm portion 12a.

Furthermore, the length of the right hand operation arm 14R in the direction along the rotational axis $O_{13}$ is shorter than the sum of the lengths of the straight arm portions 12a and 10b. Furthermore, the length of the grip unit 14c of the right hand operation arm 14R in the direction perpendicular to the rotational axis $O_{13}$ is shorter than twice the length of the straight arm portion 14a.

With such a configuration, the right hand operation arm 14R can be freely turned and moved along the rotational axis $O_{13}$ without interfering with the L-shaped arm 12. Furthermore, when the right hand operation arm 14R turns and moves along the rotational axis $O_{11}$ together with the L-shaped arm 12, as in the L-shaped arm 12, the right hand operation arm 14R can also be freely turned and moved without interfering with the L-shaped arm 10.

A distal end surface 14e in the distal end of the grip unit 14c in the extension direction is provided with an engagement unit 19R. The engagement unit 19R is engaged with a left hand operation arm 14L of the multi-jointed arm 3L to be mentioned below so that a relative position is fixed.

Although the shape of the engagement unit 19R is not particularly limited as long as the relative position can be fixed, in the present embodiment, as shown in FIGS. 3A and 3B, the engagement unit 19R includes a concave portion 15R and a convex portion 16R.

The concave portion 15R forms a groove with a rectangular cross section that penetrates between the side surfaces 14f and 14g of the grip unit 14c in the thickness direction. The concave portion 15R forms a concave portion to the distal end surface 14e.

The convex portion 16R penetrates between the side surfaces 14f and 14g of the grip unit 14c in the thickness direction. The convex portion 16R is a protrusion portion with a rectangular cross section that is provided near the side surface 14d of the concave portion 15R. The convex portion 16R forms a convex portion to the distal end surface 14e.

As shown in FIG. 3B, a shape of the convex portion 16R viewed from a normal direction of the distal end surface 14e is a substantially rectangular shape as a whole. However, the shape of the convex portion 16R is configured so that a corner to be a rectangular form is slightly notched in a rectangular form. The notch portion 16a formed at the same height as the distal end surface 14e is formed in one corner that is adjacent to the side surface 14g and is an opposite side of the concave portion 15R.

For this reason, by the notch portion 16a of the convex portion 16R, the stepped portion 16b is formed on the way from the side surface 14g to the side surface 14f in the vicinity of the side surface 14g.

Furthermore, in the present embodiment, an engagement sensor 18R is provided in the grip unit 14c of the back side of the convex portion 16R. The engagement sensor 18R detects the engaged state with an engagement unit 19L to be mentioned below.

When it is possible to detect the engaged state in the combination with the engagement sensor 18L, a suitable detection sensor of a contact type or a non-contact type can be adopted as the configuration of the engagement sensor 18R. As the contact type detection sensor, it is possible to adopt a pressure sensor, a sensor that detects the electrical conduction, a contact point type switch, or the like. Furthermore, as the non-contact type detection sensor, it is possible to adopt an optical sensor, a capacitance detection sensor, a magnetic detection sensor, a gyroscope sensor, or the like.

Furthermore, any one of the engagement sensors 18R and 18L may be an active sensor, and the other thereof may be a passive sensor or a detection target medium. For example, when one of the engagement sensors 18R and 18L is an optical sensor, the other thereof can adopt a detection mark capable of detecting the position using the optical sensor as the detection target medium.

Furthermore, the operator may visually confirm the engagement without providing the sensor in the engagement unit, and the engagement signal may be input to the engagement detection unit 102 via a master control unit interface (not shown).

In the present embodiment, as the engagement sensor 18R, a contact point type switch is adopted.

Furthermore, the engagement sensor 18R is electrically connected to the master control unit 100 and is configured so that it can transmit the detection signal to the master control unit 100 when a predetermined engaged state is detected (see FIG. 6).

The gripping operation unit 15 is a member that performs the operation input of the opening and closing operation of the gripping forceps of the slave manipulator 120R. In the present embodiment, for example, the gripping operation unit 15 is provided so that it can be pressed by a thumb and a forefinger when gripping the grip unit 14c with a middle finger, a third finger, and a little finger of the right hand $H_R$. The gripping operation unit 15 includes operation levers 15a and 15b that can detect a mutual opening angle with an angle detection unit (not shown).

The gripping operation unit 15 is electrically connected to the master control unit 100 and is configured so that it can transmit the detection signal of the opening angle using the angle detection to the master control unit 100 (see FIG. 6).

A schematic configuration of the multi-jointed arm 3L is substantially the same as that of the multi-jointed arm 3R. As shown in FIG. 2B, the multi-jointed arm 3L includes the first joint 5, the arm 6, the second joint 7, the arm 8, the third joint 9, the L-shaped arm 10, the fourth joint 11, the L-shaped arm 12, the fifth joint 13, and the left hand operation arm 14L (arm) from the proximal end side to the distal end side.

Hereinafter, the description will focus on the points different from multi-jointed arm 3R.

The first joint 5 of the multi-jointed arm 3L has the same configuration as the first joint 5 of the multi-jointed arm 3R. The first joint 5 of the multi-jointed arm 3L differs in that the rotational joint 5a is fixed at a position which is horizontally separated from the rotational joint 5a of the multi-jointed arm 3R by a fixed distance in the lower end portion of the main body frame 2.

A fixed position of the rotational joint 5a in the first joint 5 of the multi-jointed arm 3L to the main body frame 2 defines a fixed position of the proximal end of the multi-jointed arm 3L.

Like the case of the multi-jointed arm 3R, the detection units $E_{5a}$ and $E_{5b}$ of the multi-jointed arm 3L are electrically connected to the master control unit 100 and are configured so that they can each transmit the detection signal of the rotation angle and the translational displacement to the master control unit 100 (see FIG. 6).

The arm 6 of the multi-jointed arm 3L is the same member as the arm 6 of the multi-jointed arm 3R. The arm 6 of the multi-jointed arm 3L is connected to the linear driving joint 5b and the second joint 7.

The second joint 7 of the multi-jointed arm 3L has the same configuration as the second joint 7 of the multi-jointed arm 3R. Like the case of the multi-jointed arm 3R, in the second joint 7 of the multi-jointed arm 3L, the detection unit $E_7$ is electrically connected to the master control unit 100 and is configured so that it can transmit the detection signal of the translational displacement to the master control unit 100 (see FIG. 6).

The arm 8 of the multi-jointed arm 3L is the same member as the arm 8 of the multi-jointed arm 3R. The arm 8 of the multi-jointed arm 3L is connected to the second joint 7 and the third joint 9.

The third joint 9 of the multi-jointed arm 3L has the same configuration as the third joint 9 of the multi-jointed arm 3R. Like the case of the multi-jointed arm 3R, in the third joint 9 of the multi-jointed arm 3L, the detection unit $E_9$ is electrically connected to the master control unit 100 and is configured so that it can transmit the detection signal of the rotation angle to the master control unit 100 (see FIG. 6).

The L-shaped arm 10 of the multi-jointed arm 3L is the same member as the L-shaped arm 10 of the multi-jointed arm 3R. The L-shaped arm 10 of the multi-jointed arm 3L is connected to the third joint 9 and the fourth joint 11.

However, the straight arm portion 10b of the L-shaped arm 10 of the multi-jointed arm 3L extends from the straight arm portion 10a to a side provided with the multi-jointed arm 3R. The L-shaped arm 10 of the multi jointed arm 3L differs in that the fourth joint 11 is connected to the distal end of the straight arm portion 10b of the L-shaped arm 10 of the multi-jointed arm 3L.

The fourth joint 11 of the multi jointed arm 3L has the same configuration as the fourth joint 11 of the multi-jointed arm 3R. Like the case of the multi-jointed arm 3R, in the fourth joint 11 of the multi-jointed arm 3L, the detection unit $E_{11}$ is electrically connected to the master control unit 100 and is configured so that it can transmit the detection signal of the rotation angle to the master control unit 100 (see FIG. 6).

The L-shaped arm 12 of the multi-jointed arm 3L is the same member as the L-shaped arm 12 of the multi-jointed arm 3R. The L-shaped arm 12 of the multi-jointed arm 3L is connected to the fourth joint 11 and the fifth joint 13.

The fifth joint 13 of the multi-jointed arm 3L has the same configuration as the fifth joint 13 of the multi-jointed arm 3R. Like the case of the multi-jointed arm 3R, in the fifth joint 13 of the multi-jointed arm 3L, the detection unit $E_{13}$ is electrically connected to the master control unit 100 and is configured so that it can transmit the detection signal of the rotation angle to the master control unit 100 (see FIG. 6).

The left hand operation arm 14L is substantially the same member as the right hand operation arm 14R of the multi-jointed arm 3R. The left hand operation arm 14L is connected to the fifth joint 13. Furthermore, the left hand operation arm 14L is a member that constitutes the distal end of the multi-jointed arm 3L when the first joint 5 is the proximal end of the multi-jointed arm 3L.

The left hand operation arm 14L is different from the right hand operation arm 14R in that an engagement unit 19L is provided instead of the engagement unit 19R of the grip unit 14c.

Furthermore, the shape of the grip unit 14c of the left hand operation arm 14L is different from that of the grip unit 14c of the right hand operation arm 14R in that it includes a suitable three-dimensional shape which is easily gripped by the left hand $H_L$ at the side surface of the back side of the side surface 14d in which the straight arm portion 14b extends. In the present embodiment, the grip unit 14c is formed in substantial plate form having substantially the same thickness as the widths of the straight arm portions 14a and 14b, and the left hand operation arm 14L is configured in a planar symmetrical shape to the right hand operation arm 14R by the replacement of the side surfaces 14f and 14g.

The engagement unit 19L is a member for being engaged so that the relative position is fixed to the right hand operation arm 14R of the multi-jointed arm 3R. The engagement unit 19L is provided on the distal end surface 14e of the left hand operation arm 14L.

The shape of the engagement unit 19L has concave and convex portions engaged with the engagement unit 19R. In the present embodiment, as shown in FIGS. 4A and 4B, a convex portion 15L and a concave portion 16L are included.

The convex portion 15L is a convex portion that is engaged with the concave portion 15R in the state of bringing the distal end surface 14e of the left hand operation arm 14L into close contact with the distal end surface 14e of the right hand operation arm 14R. The convex portion 15L forms a protrusion portion with a rectangular cross section that penetrates between the side surfaces 14f and 14g of the grip unit 14c in the thickness direction.

The concave portion 16L is a concave portion that is engaged with the convex portion 16R in the state of bringing the distal end surface 14e of the left hand operation arm 14L into close contact with the distal end surface 14e of the right hand operation arm 14R. The concave portion 16L penetrates between the side surfaces 14f and 14g in the thickness direction. The concave portion 16L is a groove portion with a rectangular cross section that is provided near the side surface 14d of the convex portion 15L.

As shown in FIG. 4B, a shape of the concave portion 16L viewed from the distal end surface 14e in the normal direction is a shape that is fitted into the convex portion 16R. That is, the shape of the concave portion 16L is a substantially rectangular shape as a whole. In a corner of the concave portion 16 L (as the rectangular shape), the protrusion portion 17 formed from the rectangular protrusion portion slightly projected into the groove at the same height as the distal end surface 14e is formed in one corner of an opposite side of the convex portion 15L adjacent to the side surface 14g.

For this reason, by the protrusion portion 17 of the concave portion 16L, the stepped portion 17a is formed on the way from the side surface 14f to the side surface 14g in the vicinity of the side surface 14g.

Furthermore, in the present embodiment, an engagement sensor 18L is provided in the grip unit 14c of the back side of the concave portion 16L. The engagement sensor 18L detects the engaged state with an engagement unit 19R.

When it is possible to detect the engaged state in the combination with the engagement sensor 18R, a suitable detection sensor of a contact type or a non-contact type like the engagement sensor 18R can be adopted as the engagement sensor 18L. For example, when the engagement sensor 18R is the active sensor, as mentioned above, the engagement sensor 18L may be the passive sensor or the detection target medium.

In the present embodiment, as the engagement sensor 18L, the detection target medium is adopted.

Furthermore, the engagement sensor 18L is electrically connected to the master control unit 100 and is configured so that it can transmit the detection signal to the master control unit 100 when a predetermined engaged state is detected (see FIG. 6).

With the configuration of the engagement units 19R and 19L, the concave portion 15R and the convex portion 15L face each other so that the respective side surfaces 14f of the right hand operation arm 14R and the left hand operation arm 14L face the same direction, and the respective distal end surfaces 14e are matched with each other so that the convex portion 16R and the concave portion 16L face each other. As a result, as shown in FIGS. 5A and 5B, it is possible to form an engaged state where the respective distal end surfaces 14e are brought into close contact with each other, and the respective side surfaces 14f and the respective side surfaces 14g are arranged with each other.

At this time, with the engagement between the concave portion 15R and the convex portion 15L and the engagement between the convex portion 16R and the concave portion 16L, the relative position perpendicular to the thickness direction of each grip unit 14c and along each distal end surface 14e is fixed.

Furthermore, with the engagement between the stepped portion 16b in the convex portion 16R and the stepped portion 17a in the protrusion portion 17, the relative position of each grip unit 14c in the thickness direction is fixed.

That is, according to the engagement units 19R and 19L, the distal end surface 14e of the right hand operation arm 14R and the distal end surface 14e of the left hand operation arm 14L come into close contact with each other in a state in which the position in an in-plane position is fixed. The degree of freedom of the relative movement between right hand operation arm 14R and the left hand operation arm 14L is set so that all six degrees of freedom are fixed.

At this time, in the present embodiment, since the engagement sensors 18R and 18L are placed to contact with each other at the positions facing each other, the steady engaged state is detected by the engagement sensors 18R and 18L.

The gripping operation unit 15 of the multi-jointed arm 3L is a member that performs the operation input of the opening and closing operation of the gripping forceps of the slave manipulator 120L, and is the same member as the gripping operation unit 15 of the multi-jointed arm 3R. However, the left hand operation arm 14L is different in that the positions of the operation levers 15a and 15b are inverted as in the positional relationship between the side surfaces 14f and 14g so as to grip the grip unit 14c with the left hand $H_L$.

For this reason, for example, the situation in which the thumb and the forefinger of the operator can each press the operation levers 15a and 15b when gripping the grip unit 14c with the middle finger, the third finger and the little finger of the left hand $H_L$ is the same as the case of the right hand operation arm 14R.

Furthermore, as in the case of the multi-jointed arm 3R, the gripping operation unit 15 of the left hand operation arm 14L is electrically connected to the master control unit 100 and is configured so that it can transmit the detection signal of the opening angle using the angle detection unit to the master control unit 100 (see FIG. 6).

Next, a configuration of the master control unit 100 will be described with reference to FIG. 6.

The functional configuration of the master control unit 100 includes a data acquisition unit 101, an engagement detection unit 102, an initial value calculation unit 103, a storage unit 104, and an input data generation portion 105.

The data acquisition unit 101 acquires joint movement amounts detected by the respective detection units $E_{5a}$, $E_{5b}$, $E_7$, $E_9$, $E_{11}$, and $E_{13}$ of the multi-jointed arms 3R and 3L in a time series (hereinafter, each is simply referred to as a joint movement amount). The data acquisition unit 101 is electrically connected to the respective detection units $E_{5a}$, $E_{5b}$, $E_7$, $E_9$, $E_{11}$, and $E_{13}$, the engagement detection unit 102, the initial value calculation unit 103, and the input data generation portion 105. Herein, the joint movement amount refers to the rotation angle or the translational displacement that is detected by the detection unit.

The master control unit 100 includes an initialization mode and an operation mode, and the transmitting place of the joint movement amount of the data acquisition unit 101 differs depending on the modes. In the initialization mode, the master control unit 100 calculates the initial values of the joint movement amount of the multi-jointed arms 3R and 3L before the operation input to the slave manipulator 120. In the operation mode, the master control unit 100 generates the input data for operating the slave manipulator 120, based on the joint movement amount of the multi-jointed arms 3R and 3L after the initialization mode is finished.

In the present embodiment, the initialization mode starts when the data acquisition unit 101 is notified of the engagement between the right hand operation arm 14R serving as the distal end of the multi-jointed arm 3R and the left hand operation arm 14L serving as the distal end of the multi-jointed arm 3L via the engagement units 19R and 19L by the engagement detection unit 102.

In the initialization mode, when acquiring a plurality of sets of the respective joint movement amounts in a time series, the data acquisition unit 101 transmits the plurality of sets of joint movement amounts to the initial value calculation unit 103.

When the initialization is finished as will be mentioned below, the operation mode is set by receiving the transmitting of the control signal from the initial value calculation unit 103.

In the operation mode, when acquiring the respective joint movement amounts in a time series, the data acquisition unit 101 sequentially transmits the joint movement amounts to the input data generation portion 105.

The engagement detection unit 102 acquires the detection signals of the engagement sensors 18R and 18L and determines the engaged state of the engagement units 19R and 19L. When it is determined that a predetermined engaged state is provided, the engagement detection unit 102 notifies the data acquisition unit 101 of the engagement completion, sets the data acquisition unit 101 to the initialization mode, and displays the message of the engagement completion of the display unit 4.

Furthermore, when the engagement is not finished, the engagement detection unit 102 displays a message of the engagement non-completion on the display unit 4.

For this reason, in the present embodiment, the engagement detection unit 102 is electrically connected to the engagement sensors 18R and 18L, the data acquisition unit 101, and the display unit 4.

The initial value calculation unit 103 calculates the initial value of the movement of the joint in the respective detection units $E_{5a}$, $E_{5b}$, $E_7$, $E_9$, $E_{11}$, and $E_{13}$ under the condition that the relative positional relationship between the right hand operation arm 14R and the left hand operation arm 14L is fixed via the engagement units 19R and 19L, based on the joint movement amount acquired by the data acquisition unit 101 in a time series.

For this reason, the initial value calculation unit 103 is electrically connected to the data acquisition unit 101. Furthermore, the initial value calculation unit 103 is electrically connected to the storage unit 104 and the display unit 4. The initial value calculation unit 103 is configured so that it can transmit and store the calculated initial value to the storage unit 104, or it can display an error message on the display unit 4 when an error occurs in the course of the calculation processing.

A method of calculating the initial value of the movement of the joint in the initial value calculation unit 103 will be described in the movement description of the master control unit 100 mentioned below.

The storage unit 104 is electrically connected to the initial value calculation unit 103 and the input data generation portion 105, and stores the initial value of the movement of the joint that is transmitted from the initial value calculation unit 103, and the input data generation portion 105 is configured so that it can read the initial value if necessary.

The input data generation portion 105 generates the input data that includes the control objective values of the position and the orientation of the gripping forceps of the slave manipulators 120L and 120R and the control objective value that controls the opening and closing operation of the gripping forceps, based on the position and the orientation of the right hand operation arm 14R of the multi-jointed arm 3R and the left hand operation arm 14L of the multi-jointed arm 3L, and the operation amount using the operation performed on the respective gripping operation units 15.

The input data generation portion 105 is electrically connected to the data acquisition unit 101, the storage unit 104, and the slave control unit 110 that performs the operation control of the slave manipulators 120R and 120L.

The input data generation portion 105 is configured so that it can perform the variable magnification of the operation amount transmitted from the respective gripping operation units 15 depending on predetermined operation sensitivity and convert the operation amount to a control objective value of the opening and closing amount of the gripping forceps.

Furthermore, the input data generation portion 105 converts the respective joint movement amounts transmitted from the data acquisition unit 101 into the joint movement amounts on a joint coordinate system based on the initial value stored in the storage unit 104. The input data generation portion 105 is configured so that it can calculate the control objective values of the position and the orientation of the gripping forceps of the slave manipulators 120L and 120R from the joint movement amount after the conversion.

The master control unit 100 includes a computer that has a CPU, a memory, an input and output interface, and an external storage device or the like. Thus, a suitable program, which performs the control and the calculation processing corresponding to each function mentioned above, is executed.

Next, the operation of the master manipulator 1 will be described based on the method of initializing the operation input device according to the present embodiment.

Figure 7:
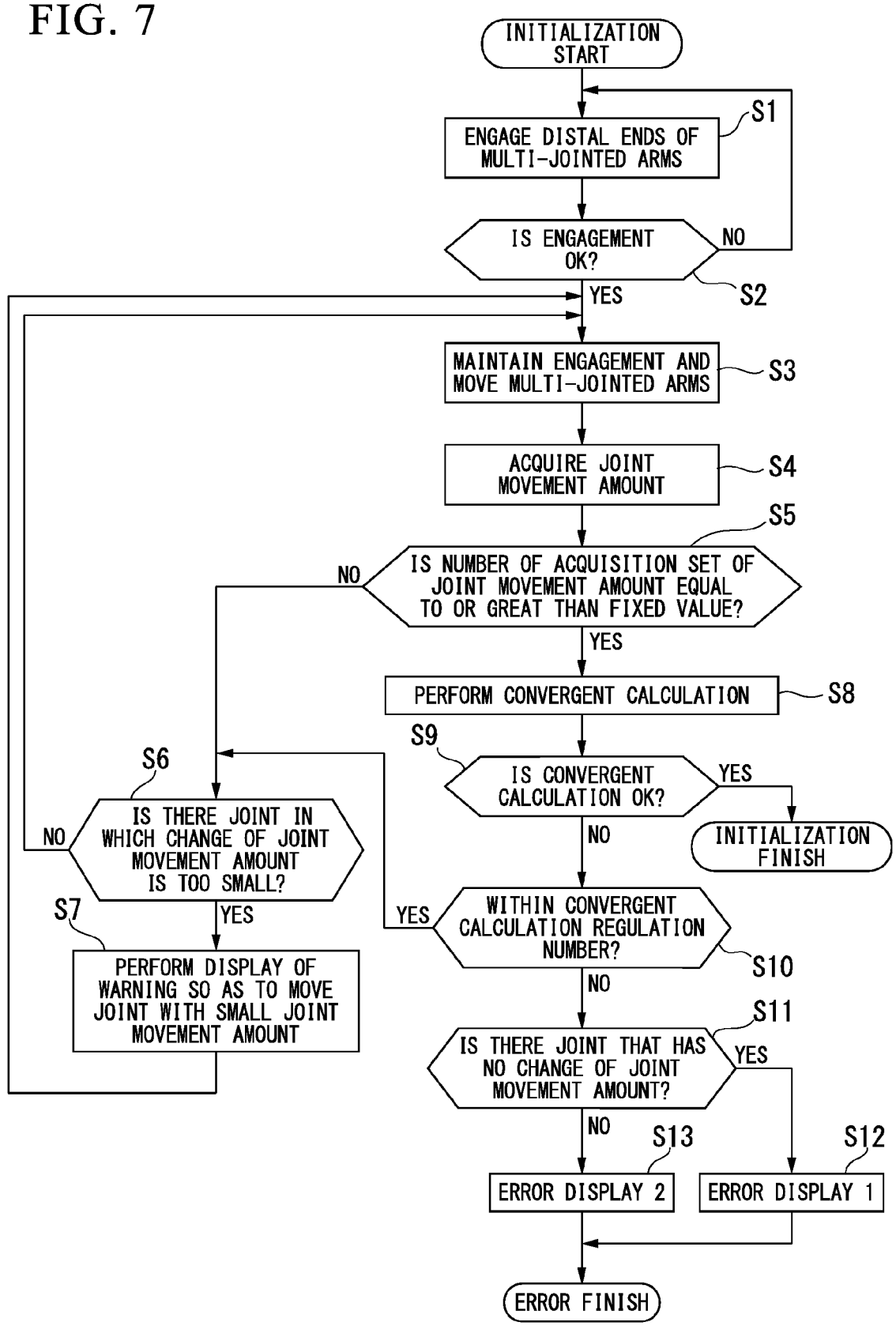
FIG. 7 is a flow chart that illustrates a method of initializing the operation input device according to the first embodiment of the present invention.
Figure 8A:
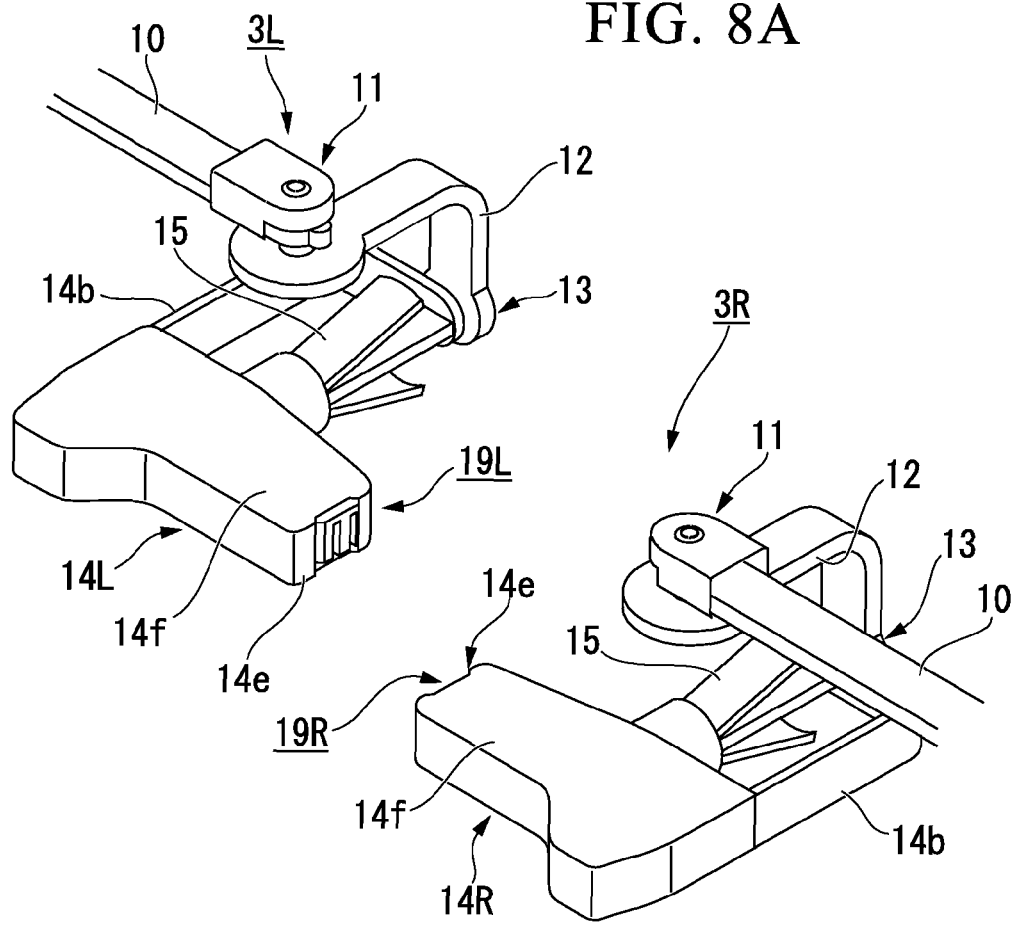
FIG. 8A is a diagram for describing an operation of an engaging process of the method of initializing the operation input device according to the first embodiment of the present invention.
Figure 8B:
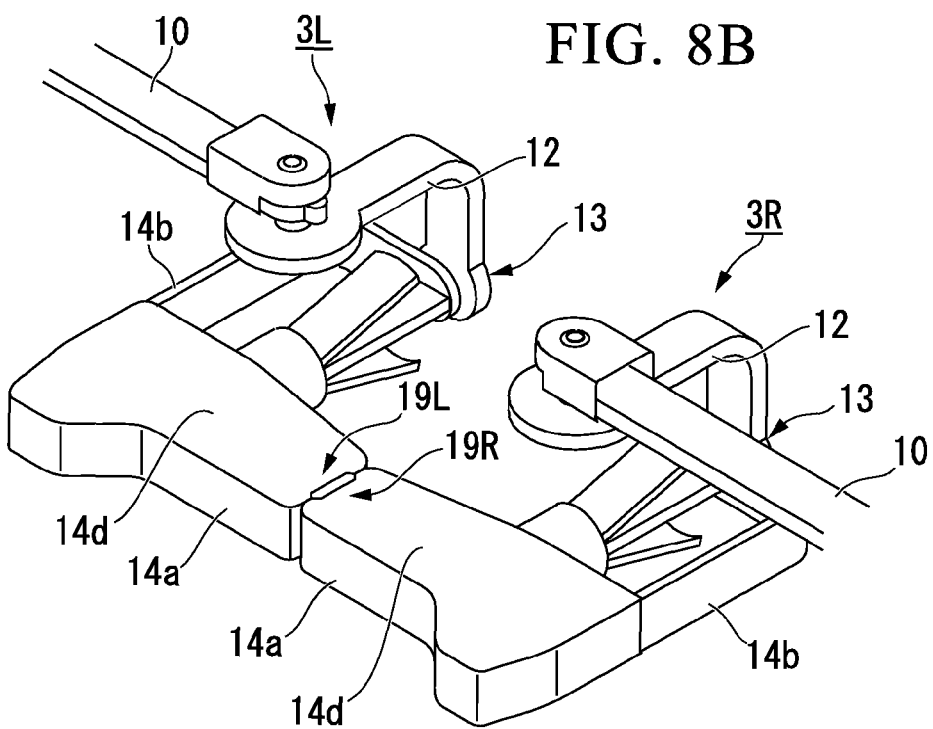
FIG. 8B is a diagram for describing the operation of the engaging process of the method of initializing the operation input device according to the first embodiment of the present invention.
Figure 9A:
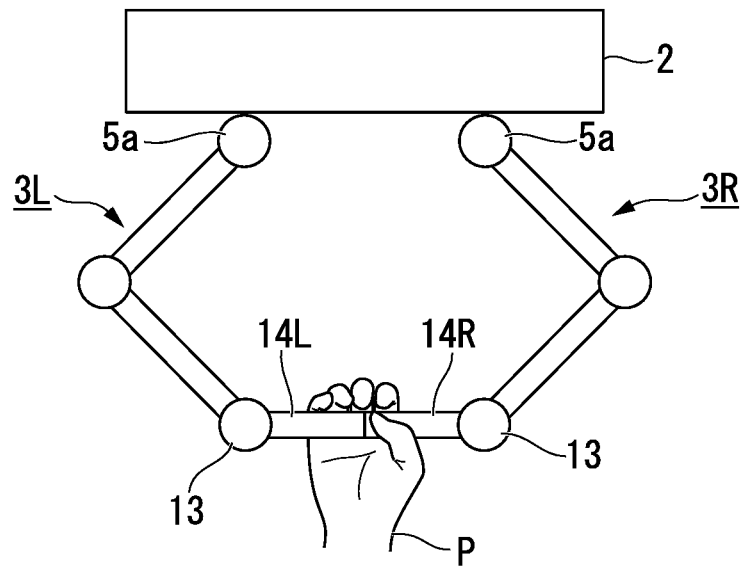
FIG. 9A is a diagram for describing an operation of a data acquisition process of the method of initializing the operation input device according to the first embodiment of the present invention.
Figure 9B:
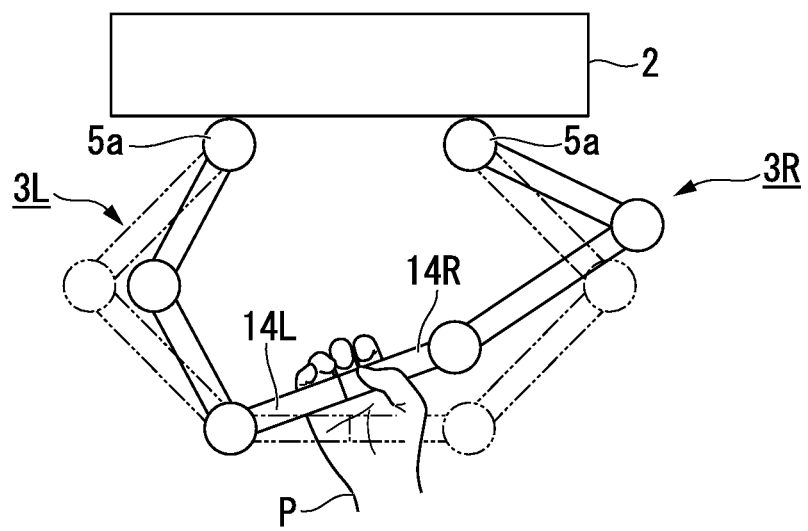
FIG. 9B is a diagram for describing the operation of the data acquisition process of the method of initializing the operation input device according to the first embodiment of the present invention.

FIG. 7 is a flow chart that illustrates the method of initializing the operation input device according to the first embodiment of the present invention. FIGS. 8A and 8B are diagrams for describing an operation of an engaging process of the method of initializing the operation input device according to the first embodiment of the present invention. FIGS. 9A and 9B are diagrams for describing an operation of a data acquisition process of the method of initializing the operation input device according to the first embodiment of the present invention.

In the master manipulator 1, increment type encoders are used as all the detection units $E_{5a}$, $E_{5b}$, $E_7$, $E_9$, $E_{11}$, and $E_{13}$. For this reason, the joint movement amount, which is output from the detection units $E_{5a}$, $E_{5b}$, $E_7$, $E_9$, $E_{11}$, and $E_{13}$, is based on an unknown initial joint value of the operation of the joint at the time of reset. For this reason, there is a need to perform the initialization operation for converting the acquired joint movement amount into the numerical value on the joint coordinate system.

The method of initializing the operation input device of the present embodiment includes sequentially performing a holding process, an engaging process, a data acquisition process, and an initial value calculation process.

The flow chart shown in FIG. 7 illustrates a flow of the method of initializing the operation input device that is performed by an operator P using the master manipulator 1 according to the present embodiment.

In addition, in the initializing method according to the present embodiment, there is an operation that is performed on the master manipulator 1 by a person, in addition to the operation that is performed by the master manipulator 1. The operation by a person may be performed by anyone, and the person may be another person that is different from the operator P who performs the operation input of the master manipulator 1 after the initialization. Hereinafter, a person who performs the initialization operation is also referred to as the operator P.

The holding process includes holding the proximal ends of the multi-jointed arms 3R and 3L in the state in which the mutual relative position is fixed.

In the present embodiment, since the respective rotational joints 5a serving as the proximal ends of the multi-jointed arms 3R and 3L are fixed at predetermined positions of the main body frame 2, the holding process is performed at the time of assembling the master manipulator 1. For this reason, the operator P does not need to perform the holding process. For this reason, in the flow chart of FIG. 7, a step corresponding to the holding process is omitted.

The fixing positions of each rotational joint 5a are stored in the storage unit 104 of the master control unit 100 as the coordinate values of the joint coordinate system that are set in the respective multi-jointed arms 3R and 3L.

However, the master manipulator 1 may have a configuration in which the operator P can change the fixed positions of the proximal ends of the multi-jointed arms 3R and 3L on the main body frame 2. In this case, there is a need to perform the holding process before step S1 of FIG. 7. That is, the operator P changes the fixed positions of the proximal ends of the multi-jointed arms 3R and 3L and renews the fixed position that is stored in the storage unit 104.

When the holding process is finished, the engaging process is performed. In the engaging process, the right hand operation arm 14R serving as the distal end of the multi-jointed arm 3R are engaged with the left hand operation arm 14L serving as the distal end of the multi-jointed arm 3L so that the relative position between them is fixed.

In the present embodiment, steps S1 and S2 constitute the engaging process.

In step S1, the operator P engages the right hand operation arm 14R with the left hand operation arm 14L via the engagement units 19R and 19L.

For example, as shown in FIG. 8A, the right hand operation arm 14R and the left hand operation arm 14L are horizontally placed so that the respective side surfaces 14f face upward, and the mutual relative position is adjusted in a positional relationship in which the engagement units 19R and 19L are engaged with each other toward a direction in which the respective distal end surfaces 14e face each other.

In the case of the present embodiment, as shown in FIG. 5A, the respective distal end surfaces 14e come into close contact with each other face to face so that the concave portion 15R faces the convex portion 15L and the convex portion 16R faces the concave portion 16L.

Moreover, as shown in FIG. 8B, the relative position between the right hand operation arm 14R and the left hand operation arm 14L in the thickness direction is adjusted, and the stepped portion 16b comes into close contact with the stepped portion 17a as shown in FIG. 5B.

Thus, the parallel movement and the rotational movement between the right hand operation arm 14R and the left hand operation arm 14L are restricted.

In this manner, step S1 is finished.

Step S2 is a step of determining whether or not the engaged state is obtained.

In the present embodiment, the detection signals from the engagement sensors 18R and 18L are acquired and the engaged state of the engagement unit 19R and 19L is determined using the engagement detection unit 102.

The engagement detection unit 102 determines the engagement completion in a case in which all the detection signals of the engagement sensors 18R and 18L express the engaged state within a permissible range of a predetermined engaged state. At this time, the engagement detection unit 102 notifies the data acquisition unit 101 of the determination result and displays the message of the engagement completion on the display unit 4.

When the data acquisition unit 101 is notified of the engagement completion, the data acquisition unit 101 is set to the initialization mode.

When it is determined that the process does not lead to the engagement completion, the message of the engagement non-completion is displayed on the display unit 4.

The operator P repeats step S1 until the engagement completion is determined, by minutely adjusting the engagement between the engagement units 19R and 19L, trying the engagement again or the like in the case of the engagement non-completion after viewing the display of the display unit 4.

In this manner, step S2 is finished.

Next, the data acquisition process is performed. The data acquisition process includes acquiring a plurality of sets of the joint movement amount in a time series from the respective detection units $E_{5a}$, $E_{5b}$, $E_7$, $E_9$, $E_{11}$, and $E_{13}$ provided in the respective joints of the mutually engaged multi jointed arms 3R and 3L while moving the mutually engaged right hand operation arms 14R and the left hand operation arm 14L. In the present embodiment, steps S3 to S7 constitute the data acquisition process.

Step S3 is a step in which the engagement between the right hand operation arm 14R and the left hand operation arm 14L is maintained by the operator P to suitably move the multi-jointed arms 3R and 3L.

After the engaging process is finished, as schematically shown in FIG. 9A, the multi-jointed arms 3R and 3L constitute a closed link loop since the respective rotational joints 5a are fixed to the main body frame 2.

After the engaging process is finished, the data acquisition unit 101 immediately transmits the reset signal to the respective detection units $E_{5a}$, $E_{5b}$, $E_7$, $E_9$, $E_{11}$, and $E_{13}$. Thus, all the joint movement amounts of the respective detection units $E_{5a}$, $E_{5b}$, $E_7$, $E_9$, $E_{11}$, and $E_{13}$ are reset to 0.

In this state, the operator P holds the right hand operation arms 14R and the left hand operation arm 14L with a hand, suitably engages them with each other, and moves the arms. Thus, as schematically shown by a solid line in FIG. 9B, the respective joints and the respective arms of the multi-jointed arms 3R and 3L are moved within each movable range.

Next, in step S4, the joint movement amounts are acquired in a time series from the respective detection units $E_{5a}$, $E_{5b}$, $E_7$, $E_9$, $E_{11}$ and $E_{13}$ using the data acquisition unit 101. The respective acquired joint movement amounts are stored in the data acquisition unit 101. A time interval of acquiring the joint movement amount is set to a constant value, for example, 0.5 seconds.

Hereinafter, a transmitting time of the reset signal is set to t=0, and the joint movement amounts using the respective detection units $E_{5a}$, $E_{5b}$, $E_7$, $E_9$, $E_{11}$, and $E_{13}$ at the time t are expressed by $e_{Rj}(t)$ and $e_{Lj}(t)$ (herein, j=1, ..., 6).

However, since the reset is performed as mentioned above, the following equations (1a) and (1b) hold:

$$e_{Rj(0)}=0 (j=1,\ldots,6) \tag{1a}$$

$$e_{Lj(0)}=0 (j=1,\ldots,6) \tag{1b}$$

In addition, in the present embodiment, in order to solve a simultaneous equation, there is a need for the number of the acquisition sets that is greater than or equal to an unknown number. Since there are twelve unknown numbers (joint numbers), the joint movement amount is acquired until at least t=12.

In this manner, step S4 is finished.

Herein, the meaning of the additional characters will be described. Unless the characters are particularly defined, such additional characters are also used with a common meaning in other variables to be mentioned below.

The additional character R indicates one connected with the multi-jointed arm 3R. The additional character L indicates one connected with the multi-jointed arm 3L.

The additional character j indicates that 1, 2, 3, 4, 5, and 6 are each connected with the detection units $E_{5a}$, $E_{5b}$, $E_7$, $E_9$, $E_{11}$, and $E_{13}$. Furthermore, the additional character j indicates that 1, 2, 3, 4, 5, and 6 are connected with the rotational joint 5a, the linear driving joint 5b, the second joint 7, the third joint 9, the fourth joint 11, and the fifth joint 13.

Next, in step S5, it is determined whether or not the engagement unit is sufficiently operated. When only the position of the engagement unit is moved but the orientation thereof is not moved, or when there is only the movement of the same pattern, precision is not accomplished. For this reason, kinematics are solved using $e_{Rj(t)}$ and $e_{Lj(t)}$ (herein, j=1, ..., 6) to compute a temporary position orientation.

Every moment change of the temporary position orientation is discriminated and when the change does not exceed a prescribed value, the process moves to step S6. When the value of the temporary position orientation is sufficiently changed, the data acquisition unit 101 transmits the plurality of sets of joint movement amounts to the initial value calculation unit 103 and the process moves to step S8. Thus, the data acquisition process is finished.

In step S6, the data acquisition unit 101 determines whether or not there is a joint that has too little change of the joint movement amount.

That is, the data acquisition unit 101 calculates a change width of the joint movement amount of the respective joints. When there is a joint that has a changed width smaller than a prescribed allowance range, the process moves to step S7.

When there is no joint that has the change width smaller than the allowance range, the process moves to step S3, and steps S3 to S5 are repeated.

In step S7, the data acquisition unit 101 displays the message of warning to move the joint having the little joint movement amount on the display unit 4.

When step S7 is finished, the process moves to step S3, and step S3 to step S6 are repeated.

When there is a joint that has too little change of the joint movement amount, the joint becomes a factor in which an error of an unknown number calculated in the initial value calculation process increases.

In the present embodiment, by providing step S7, when the operator P performs a moving method in which the change of the joint movement amount of a partial joint is too little, the operator P can know the moving method via the display unit 4. Thus, the operator P can improve the moving method of the right hand operation arm 14R and the left hand operation arm 14L, and thus accuracy of the initialization can be improved.

In steps S8 and S9, the initial value calculation process is performed using the initial value calculation unit 103.

The initial value calculation process includes calculating an unknown initial joint value under the condition that the relative positional relationship between the right hand operation arm 14R and the left hand operation arm 14L is fixed by the engagement, based on the joint movement amount that is acquired in a time series in the data acquisition process.

When expressing the operation of each joint by $\theta_{Rj(t)}$, $\theta_{Lj(t)}$ (herein, $j=1, \ldots, 6$) using the joint coordinate system, the following equations (2a) and (2b) hold:

$$\theta_{Rj(t)} = \theta_{Rj(0)} + e_{Rj(t)} (j=1, \ldots, 6) \quad (2a)$$

$$\theta_{Lj(t)} = \theta_{Lj(0)} + e_{Lj(t)} (j=1, \ldots, 6) \quad (2b)$$

Herein, $\theta_{Rj(0)}$ and $\theta_{Lj(0)}$ are the initial values of the operation of each joint at the time of reset. $\theta_{Rj(0)}$ and $\theta_{Lj(0)}$ are information that is not provided from the respective detection units, and thus are unknown numbers.

Generally, when six-dimensional vector (twist) is $v$ in which a velocity vector $v$ and an angular velocity vector $\omega$ in the joint coordinate system are arranged, a relationship between $v$ and the velocity $\theta'$ (the symbol ' shows a temporal differentiation) can be expressed by the following equation (3) using a basic Jacobian matrix $J_{B(\theta)}$:

$$v = J_{B(\theta)} \theta' \quad (3)$$

Since the joint links are connected to each other in a chain form and the places near the joint links are restricted, the velocities of each joint can be sequentially calculated from the root. Since the velocity of the joint link i is one in which a new term added by the joint i is added to the velocity of the link i−1, the velocity v and the angular velocity $\omega$ of the joint coordinate $\{O_n\}$ are expressed by the following equation (4) (wherein, $n=6$):

$$\begin{bmatrix} v \\ \omega \end{bmatrix} = \sum_{i=1}^{n} \begin{bmatrix} v_i \\ \omega_i \end{bmatrix} = [J_{B1} \quad J_{B2} \quad \ldots \quad J_{Bn}] \begin{bmatrix} \theta'_1 \\ \theta'_2 \\ \vdots \\ \theta'_n \end{bmatrix} \quad (4)$$

When collecting the equation using the following equations (5), (6), and (7), the relationship between the velocity of each joint, the velocity and the angular velocity of the frame $\{O_n\}$ is expressed by the following equation (8) using a basic Jacobian matrix $J_{B(\theta)}$:

$$v = \begin{bmatrix} v \\ \omega \end{bmatrix} \quad (5)$$

$$J_{B(\theta)} = [J_{B1} \quad J_{B2} \quad \ldots \quad J_{Bn}] \quad (6)$$

$$\theta' = \begin{bmatrix} \theta'_1 \\ \theta'_2 \\ \vdots \\ \theta'_n \end{bmatrix} \quad (7)$$

$$v = J_{B(\theta)} \theta' \quad (8)$$

Meanwhile, in the right hand operation arm 14R and the left hand operation arm 14L, when the twists of the mutually engaged point are $v_R$ and $v_L$, the following equations (9a) and (9b) are expressed.

Herein, the symbol [6,1] shows a 6×1 matrix. Hereinafter, [n,m] shows an n×m matrix (n and m are positive integers).

$$v_R[6,1] = J_{BR}[6,6] \theta_R'[6,1] \quad (9a)$$

$$v_L[6,1] = J_{BL}[6,6] \theta_L'[6,1] \quad (9b)$$

Since both $\theta_R[6,1]$ and $\theta_L[6,1]$ acquired by the data acquisition unit 101 are acquired under the condition that the relative positional relationship between the right hand operation arm 14R and the left hand operation arm 14L is fixed by the engagement, $v_R[6,1]$ is equal to $v_L[6,1]$. For this reason, it is necessary that the following equation (10) hold:

$$J_{BR}[6,6] \theta_R'[6,1] = J_{BL}[6,6] \theta_L'[6,1] \quad (10)$$

The unknown numbers $\theta_{Rj}(0)$ and $\theta_{Lj}(0)$ ($j=1, \ldots, 6$) are obtained by solving the equation (10).

In the present embodiment, a residual error $f(\theta_i)[6,1]$ is considered as the following equation (11) and the convergent calculation of $f(\theta_i)[6,1]=0$ to find $\theta_i$.

In addition, in the present embodiment, whenever step S8 is performed after the initialization starts, a counter which stores the number of times step S8 is performed is renewed.

$$f(\theta_i)[6,1] = J_{BR}[6,6] \theta_R'[6,1] - J_{BL}[6,6] \theta_L'[6,1] \quad (11)$$

$$\theta_i = [\theta_{R1(0)} \ldots \theta_{R6(0)} \theta_{L1(0)} \ldots \theta_{L6(0)}] \quad (12)$$

Specifically, the residual error $f(\theta_i)[6,1]$ becomes a simultaneous equation in which $\theta_i$ is an unknown number. The initial value calculation unit 103 momently calculates $\theta_i$ in a well-known sequence using an iterative least squares technique that is an approximate method of the simultaneous equation. Furthermore, the result is substituted for the equation (11), the residual error $f(\theta_i)[6,1]$ is calculated, and the norm of $f(\theta_i)[6,1]$ is calculated.

In this manner, step S8 is finished.

Next, in step S9, the initial value calculation unit 103 determines whether or not the convergent calculation is convergent. That is, the initial value calculation unit 103 determines that the convergence is completed when the norm of $f(\theta_i)[6,1]$ has a value that is less than a convergent determination value $\epsilon$ that is set in advance.

The initial value calculation unit 103 transmits $\theta_i$ calculated when the convergence is completed to the storage unit 104, releases the initialization mode of the data acquisition unit 101, and sets the data acquisition unit 101 to the operation mode. Thus, the initialization is finished.

When the initialization is finished, since the data acquisition unit 101 is changed to the operation mode, the joint movement amount acquired by the data acquisition unit 101 is transmitted to the input data generation portion 105.

The input data generation portion 105 adds the initial value of the operation of the joint stored in the storage unit 104 to the joint movement amount transmitted from the data acquisition unit 101 using the equations (2a) and (2b) to generate $\theta_{R_j}(t)$ and $\theta_{L_j}(t)$.

Thus, the positions and the orientations of each joint of the multi-jointed arms 3R and 3L are settled. For this reason, the input data generation portion 105 generates the input data including the control objective values of the positions and the orientations of the gripping forceps of the slave manipulators 120L and 120R and the control objective value for controlling the opening and closing operation of the gripping forceps, based on the positions and the orientations of the right hand operation arm 14R and the left hand operation arm 14L and the operation amount due to the operation accomplished for the respective gripping operation units 15, and transmits the input data to the slave control unit 110.

The slave control unit 110 drives the slave manipulators 120R and 120L based on the transmitted input data. In this manner, the operation input using the master manipulator 1 is transmitted to the slave manipulators 120R and 120L.

In step S10, the initial value calculation unit 103 compares the number of times step S8 is performed to a prescribed convergent calculation regulation number with reference to the counter so as to determine the processing of a case in which the convergence is not completed.

When the number of times step S8 is performed is within the convergent calculation regulation number, in order to execute the data acquisition process and the initial value calculation process again, the process moves to step S3.

When the number of times step S8 is performed exceeds the convergent calculation regulation number, the process moves to step S11.

In step S11, the initial value calculation unit 103 determines whether or not there is a joint without a change of the joint movement amount with reference to the time-series change of the joint movement amount used in the convergent calculation.

When step S11 is reached, even if the data acquisition process is performed after performing the warning when there are few changes in the joint movement amount, the convergence cannot be completed within the convergent calculation regulation number. When reaching step S11, it is highly possible that the joint is not operated or the joint movement amount reflecting the operation of the joint cannot be acquired due to breakdown of a particular joint or the detection unit.

When there is a joint without change of the joint movement amount, since it is highly possible that the joint or the detection unit is out of order, the process moves to step S12.

When there is no joint without change of the joint movement amount, although the joint movement amount is changed, since the joint movement amount is more likely to be incorrect and the joint cannot be specified, the process moves to step S13.

In step S12, the initial value calculation unit 103 specifies the joint without change of the joint movement amount, displays a message (error display 1) to the effect that the joint may be out of order, performs the warning and finishes the operation.

In addition, a method of warning is not limited to the warning message mentioned above, warning using the image and the blinking of light may be used, and the warning may be performed by a voice or a warning sound.

In step S13, the initial value calculation unit 103 displays a message (error display 2) to the effect that an incorrect joint movement amount may be output although it is unknown which joint it is, performs the warning, and finishes the operation. In addition, as in step S12, a method of warning is not limited to the warning message as mentioned above, warning using the image and the blinking of light may be used, and warning using a sound (including a warning sound) may be performed.

Thus, since the operator P can obtain a suggestion concerning the error finishing of the initialization and the possibility of the breakdown using the display of the display unit 4, check and repair can be performed based on the respective error displays.

In this manner, according to the master manipulator 1 according to the present embodiment, the right hand operation arm 14R and the left hand operation arm 14L are moved in a state of engaging the engagement units 19R and 19L provided in the right hand operation arm 14R and the left hand operation arm 14L, the joint movement amounts are acquired from the detection units of each joint in a time series, an unknown initial joint value is calculated under the condition that the relative positional relationship between the right hand operation arm 14R and the left hand operation arm 14L is fixed via the engagement unit, and the initialization can be performed. For this reason, it is possible to perform the initialization without providing a positioning member that is used in the initialization in the operation range of the master manipulator 1.

As a consequence, since the operation range of the master manipulator 1 is not limited by the positioning member or the like, it is possible to perform the operation input in a more extensive space. Furthermore, since there is no limit of the operation range of the slave manipulator 120 accompanied by the limit of the range of the operation input, the operation range of the slave manipulator 120 is also expanded.

Furthermore, since the positioning member may not be provided, a simple configuration can be realized.

First Modified Example

Next, an operation input device according to a modified example (first modified example) of the present embodiment will be described.

Figure 10:
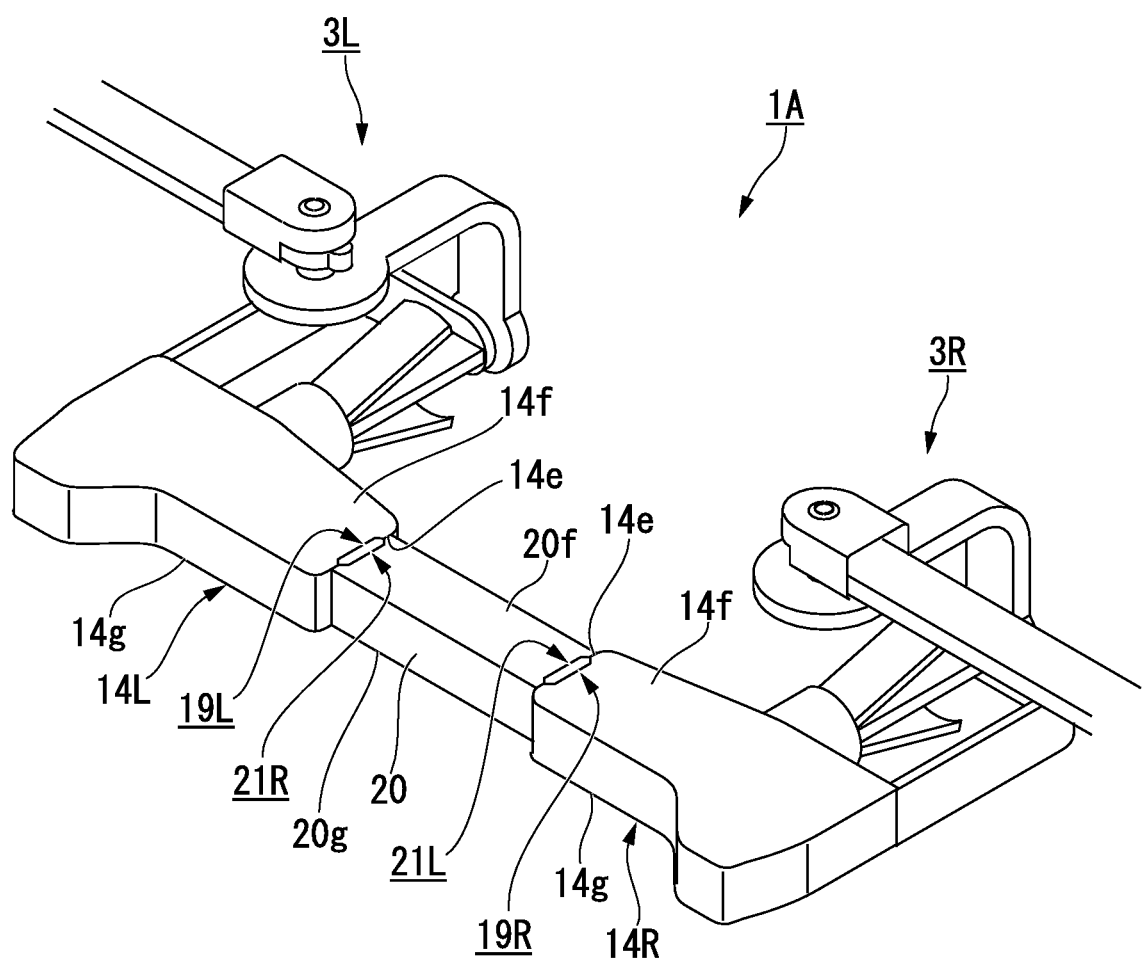
FIG. 10 is a schematic perspective view that illustrates a configuration of main parts of an operation input device according to a modified example (first modified example) of the first embodiment of the present invention.
Figure 11:
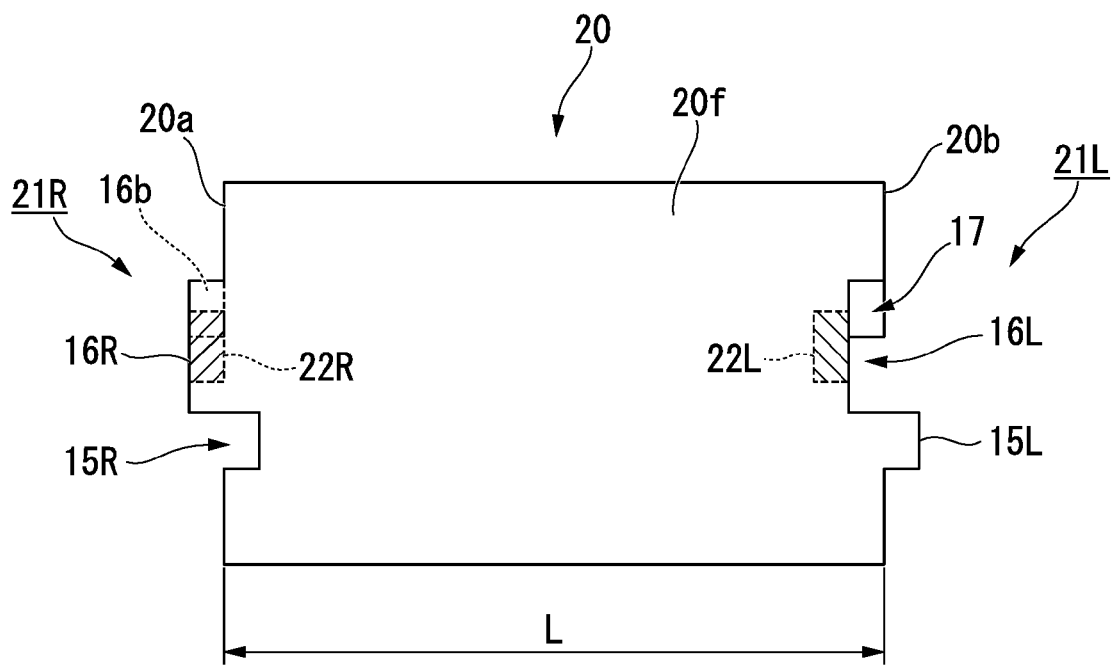
FIG. 11 is a plan view of an intermediate member that is used in the operation input device according to the modified example (first modified example) of the first embodiment of the present invention.

FIG. 10 is a schematic perspective view that illustrates a configuration of a main part of the operation input device according to the modified example (first modified example) of the first embodiment of the present invention. FIG. 11 is a plan view of an intermediate member that is used in the operation input device according to the modified example (first modified example) of the first embodiment of the present invention.

FIG. 10 illustrates a configuration of the main part of a master manipulator 1A (operation input device) according to the present modified example.

The master manipulator 1 according to the first embodiment is an example of a case in which the engagement units 19R and 19L directly engage the right hand operation arm 14R and the left hand operation arm 14L to fix the mutual relative position. However, a master manipulator 1A according to the present modified example differs in that the engagement units are configured so as to be engaged with the engagement units of the multi jointed arms of the engagement target via an intermediate member 20 that constantly maintains the distance between the multi jointed arms of the engagement target and the engagement units.

For this reason, other configurations than the intermediate member 20 can adopt the same configurations as in the master manipulator 1. Hereinafter, the points different from the first embodiment will be mainly described.

As shown in FIG. 11, the intermediate member 20 is a member in which facing end portion side surfaces 20a and 20b of a rectangular plate having the same thickness as the right hand operation arm 14R and the left hand operation arm 14L are each formed with engagement units 21R and 21L. A distance between the end portion side surfaces 20a and 20b is defined L.

The engagement unit 21R has a configuration in which the engagement sensor 18R is replaced with the detection target medium 22R to the engagement sensor 18L by the engagement unit 19R in the first embodiment.

The engagement unit 21L has a configuration in which the engagement sensor 18L is replaced with the detection target medium 22L to the engagement sensor 18R by the engagement unit 19L in the first embodiment.

However, the side surfaces 14f and 14g in the right hand operation arm 14R and the left hand operation arm 14L have the configurations each corresponding to the side surfaces 20f and 20g (see FIG. 10) of the intermediate member 20 in the plate thickness direction.

With such a configuration, the engagement unit 19L and the engagement unit 21R can be engaged with each other similarly to the engagement units 19L and 19R, and the engaged state can be detected by the engagement sensor 18L.

Furthermore, the engagement unit 21L and the engagement unit 19R can be engaged with each other similarly to the engagement units 19L and 19R, and the engaged state can be detected by the engagement sensor 18R.

Next, the initializing method of the master manipulator 1A will be described based on the points different from the first embodiment.

The initializing method of the master manipulator 1A of the present embodiment can be performed in substantially the same manner as the initializing method of the first embodiment in accordance with the flow chart of FIG. 7.

However, the method differs in that the right hand operation arm 14R and the left hand operation arm 14L are engaged with each other via the intermediate member 20 in the engaging process (steps S1 and S2).

For this reason, the left hand operation arm 14L and the right hand operation arm 14R are engaged with each other at a position separated by a distance L in the normal direction of the distal end surface 14e via the intermediate member 20.

According to the present modified example, as in the first embodiment mentioned above, the initialization can be performed.

In the present modified example, since the arms are engaged with each other via the intermediate member 20, even in a case in which there is a shape in which the right hand operation arm 14R and the left hand operation arm 14L are hard to engage directly, or there is a shape in which, although the arms can be directly engaged with each other, it is hard for the operator P to hold the right hand operation arm 14R and the left hand operation arm 14L by hand and move, the arms can be easily engaged with each other or the arms can be easily moved after the engagement by suitably setting the shape of the intermediate member 20.

Furthermore, in the present modified example, since there is no need to perform the output of the engagement completion on the master control unit 100 from the intermediate member 20 by providing the target detection media 22R and 22L in the intermediate member 20, the configuration of the intermediate member 20 is simplified.

Second Embodiment

An operation input device according to a second embodiment of the present embodiment will be described.

Figure 12A:
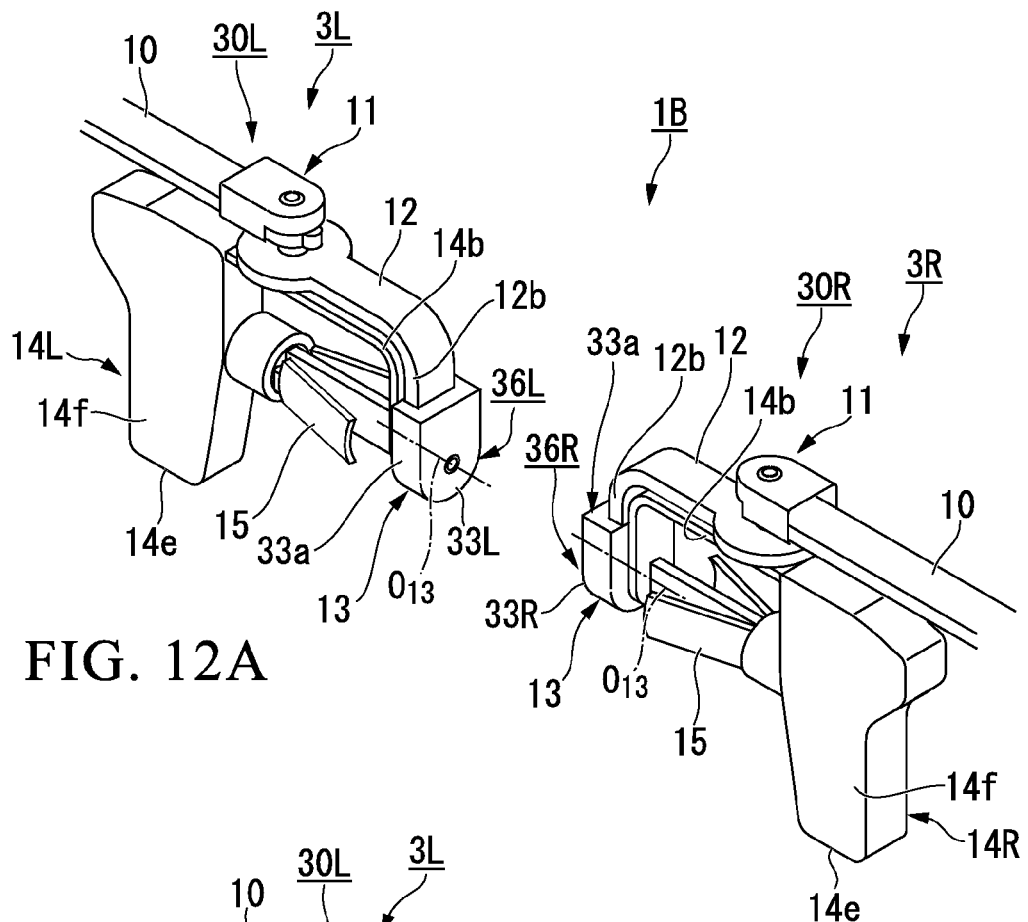
FIG. 12A is a schematic perspective view that illustrates a configuration of main parts of an operation input device according to a second embodiment of the present invention.
Figure 12B:
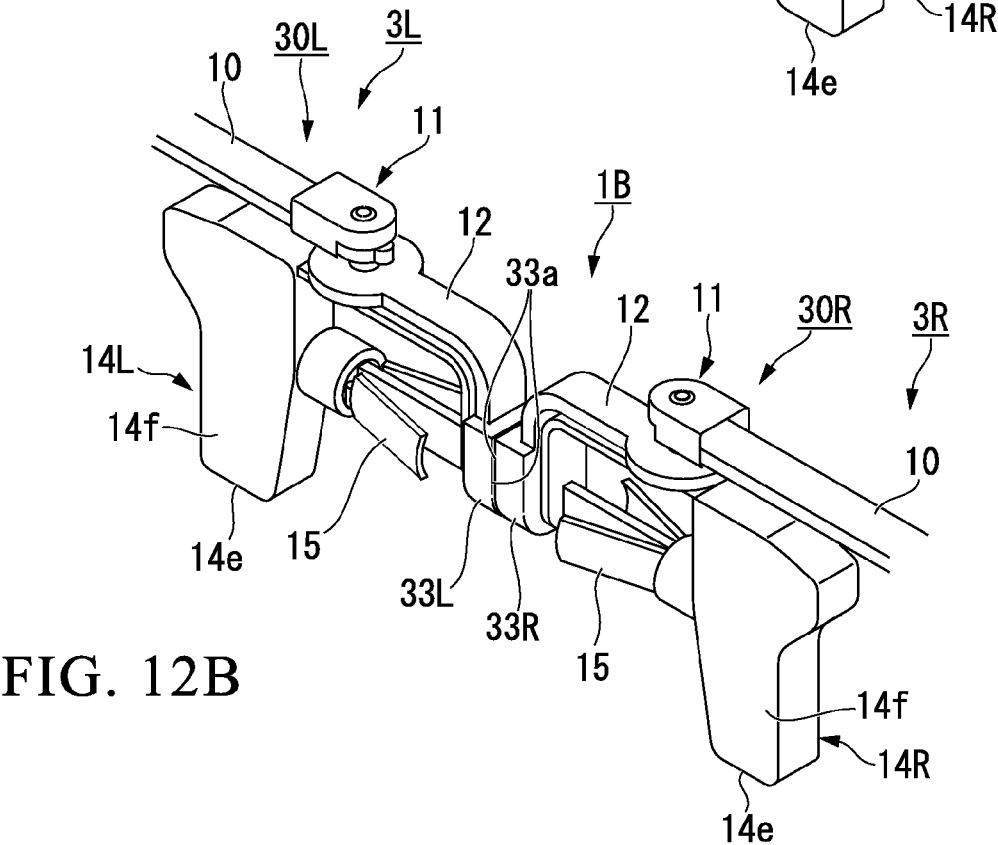
FIG. 12B is a diagram for describing an operation of the operation input device according to the second embodiment of the present invention.
Figure 13A:
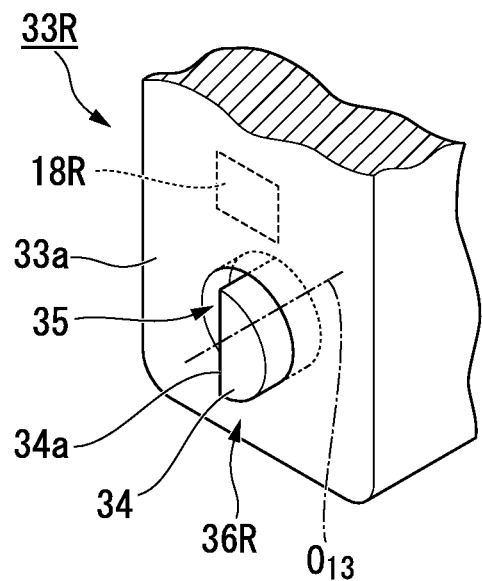
FIG. 13A is a schematic perspective view that illustrates a configuration of an engagement unit of the operation input device according to the second embodiment of the present invention.
Figure 13B:
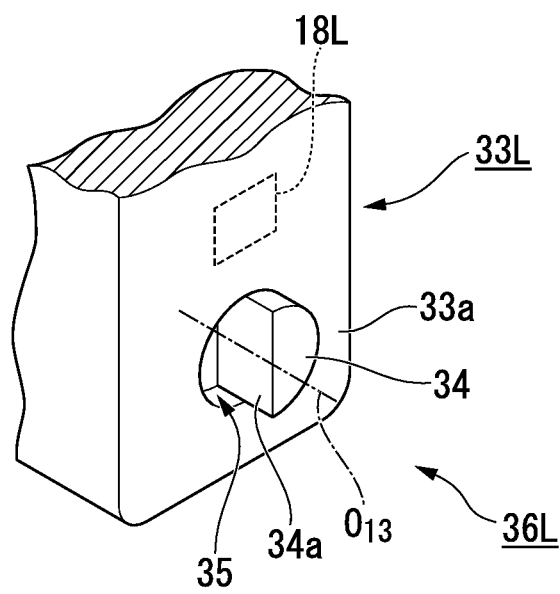
FIG. 13B is a schematic perspective view that illustrates a configuration of an engagement unit of the operation input device according to the second embodiment of the present invention.

FIGS. 12A and 12B are a schematic perspective view and a diagram for describing an operation that illustrate the configuration of the main parts of the operation input device according to the second embodiment of the present invention. FIGS. 13A and 13B are schematic perspective views that illustrate a configuration of an engagement unit of the operation input device of the second embodiment of the present invention.

In a master manipulator 1B (operation input device) according to the present embodiment, the engagement units 19R and 19L of the master manipulator 1 according to the first embodiment are omitted as the main parts thereof are shown in FIG. 12A, and a detection unit $F_{13}$ (see FIG. 6) capable of detecting an absolute rotation angle from the reference of the joint coordinate system is included instead of the respective detection units $E_{13}$. The master manipulator 1B has a configuration in which connection units 33R and 33L and engagement units 36R and 36L are added to the L-shaped arm 12.

The configuration of the multi jointed arm 3R (3L) according to the present embodiment can be divided into the right hand operation arm 14R (left hand operation arm 14L) and the fifth joint 13, neither of which requires the initialization, and the multi jointed arm unit 30R (30L) (multi-jointed arm) that includes the rotational joint 5a, the linear driving joint 5b, the arm 6, the second joint 7, the arm 8, the third joint 9, the L-shaped arm 10, the fourth joint 11, and the L-shaped arm 12 and requires the initialization.

Hereinafter, the points different from the first embodiment will be mainly described.

The connection unit 33R is a member that is provided at a side surface opposite to the side surface facing the straight arm portion 14b in the straight arm portion 12b of the L-shaped arm 12 of the right hand operation arm 14R. As shown in FIG. 13A, the connection unit 33R includes a contact surface 33a perpendicular to the rotational axis $O_{13}$.

Furthermore, the connection unit 33L is a member that is provided at a side surface opposite to the side surface facing the straight arm portion 14b in the straight arm portion 12b of the L-shaped arm 12 of the left hand operation arm 14L. As shown in FIG. 13B, the connection unit 33L includes a contact surface 33a perpendicular to the rotational axis $O_{13}$.

On the contact surface 33a of the connection unit 33R, an engagement unit 36R is provided which fixes the relative positional relationship between the connection unit 33R and the connection unit 33L when bringing the contact surface 33a into contact with the contact surface 33a of the connection unit 33L.

Furthermore, on the contact surface 33a of the connection unit 33L, an engagement unit 36L is provided which fixes the relative positional relationship between the connection unit 33L and the connection unit 33R when bringing the contact surface 33a into contact with the contact surface 33a of the connection unit 33R.

In the present embodiment, the positions of the engagement units 36R and 36L are provided on the rotational axis $O_{13}$ as an example.

In this manner, the engagement unit 36R (36L) is provided in the connection unit 33R (33L) of the straight arm portion 12b corresponding to the distal end of the multi jointed arm unit 30R (30L).

The engagement unit 36R includes a semicircular protrusion portion 34 that protrudes in a direction along the rotational axis $O_{13}$ from the contact surface 33a and uses the rotational axis $O_{13}$ as a central axis, and a semicircular hole portion 35 that is adjacent to the protrusion portion 34, is dented in the direction along the rotational axis $O_{13}$ from the contact surface 33a, and uses the rotational axis $O_{13}$ as the central axis. Furthermore, an outer diameter of the protrusion portion 34 is identical to an inner diameter of the hole portion 35, and a protruding height of the protrusion portion 34 is smaller than a depth of the hole portion 35.

Furthermore, on a boundary between the protrusion portion 34 and the hole portion 35, an engagement surface 34a that is a plane along a longitudinal direction of the straight arm portion 12b and the rotational axis $O_{13}$ extends from the distal end of the protrusion portion 34 to the lower surface of the hole portion 35.

The engagement unit 36L is provided with the protrusion portion 34 and the hole portion 35 having the same position and shape as the engagement unit 36R on the contact surface 33a of the connection unit 33L.

With the configurations of the engagement units 36R and 36L, when the respective contact surfaces 33a face each other, and the respective protrusion portions 34 of the engagement units 36R and 36L are inserted into the respective counterpart hole portions 35 in a state in which the mutual engagement surfaces 34a are matched, the respective contact surfaces 33a can be engaged with each other so as to come into close contact with each other.

The same engagement sensors 18R and 18L as the first embodiment are provided near the engagement units 36R and 36L at the positions facing each other in the engaged state.

For this reason, the engaged state can be detected by the engagement sensors 18R and 18L.

According to the master manipulator 1B according to the present embodiment, since the increment type encoder is used in each joint of the multi jointed arm units 30R and 30L as in the first embodiment, the initialization is required.

The method of initializing the manipulator 1B according to the present embodiment can be performed in accordance with the flow chart of FIG. 7 in substantially the same manner as the initializing method according to the first embodiment mentioned above.

However, the method differs in that the multi jointed arm units 30R and 30L are initialized, and the engagement units 36R and 36L provided in the distal ends of the multi jointed arm units 30R and 30L are engaged with each other in the engaging process (steps S1 and S2).

Hereinafter, the points different from the first embodiment will be mainly described.

As shown in FIG. 12A, in the engaging process according to the present embodiment, the connection units 33R and 33L hold the right hand operation arm 14R and the left hand operation arm 14L in a positional relationship in which the mutual contact surfaces 33a and the engagement units 36R and 36L face each other, position the arms so that the respective rotational axes $O_{13}$ are coaxial, bring the contact surfaces 33a into close contact with each other, and engage the engagement units 36R and 36L. Thus, as shown in FIG. 12B, the engaged state is realized.

In the engaged state, since the engagement sensors 18R and 18L face each other and come into close contact with each other, the engagement can be detected.

At this time, in the present embodiment, there is no need to particularly position the positions of the respective fifth joints 13.

The engagement units 36R and 36L according to the present embodiment are able to perform the engagement and disengagement only by the movement in a direction along the rotational axis $O_{13}$, and thus, the tasks of the engagement and the disengagement are facilitated. Furthermore, it is easy to maintain the engaged state.

In the data acquisition process, the present embodiment is different in that the multi jointed arm units 30R and 30L are moved with the L-shaped arms 12 of the mutually engaged state in step S3.

Furthermore, the present embodiment is different in that the joint movement amounts of the respective detection units $E_{5a}$, $S_{5b}$, $E_7$, $E_9$, and $E_{11}$ are acquired in step S4.

In the initial value calculation process, the additional character j is 1 to 5 in each equation, only the specific form of the matrix is different, and the initial value can be calculated by substantively the same convergent calculation.

In this manner, the present embodiment is substantially the same as the first embodiment mentioned above, and the initialization of the multi jointed arm units 30R and 30L can be performed.

The present embodiment is an example in which, although there is a need to initialize the multi jointed arms, in a part of the multi-jointed arms, the engagement unit may be provided in the distal end of the multi jointed arm portion requiring the initialization.

Third Embodiment

An operation input device according to the third embodiment of the present invention will be described.

Figure 14A:
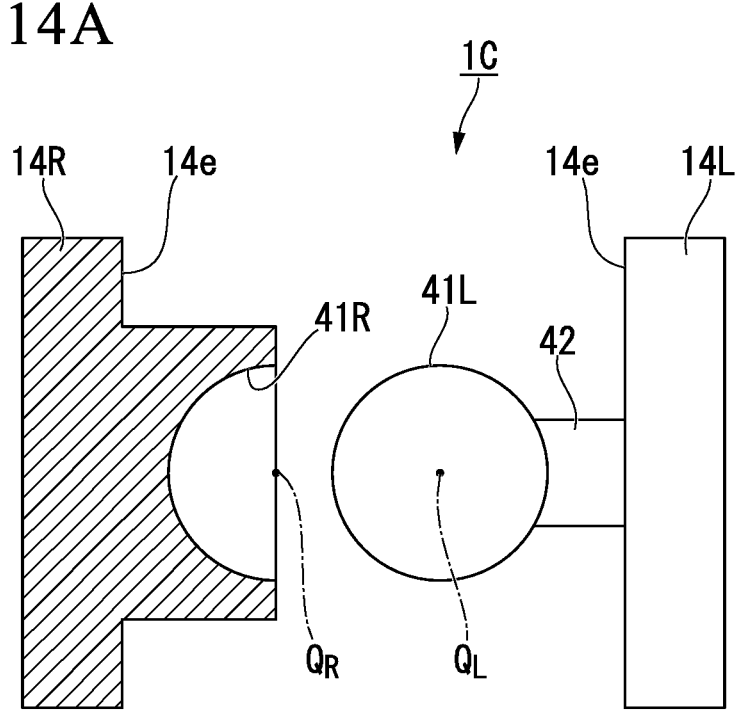
FIG. 14A is a partially schematic cross-sectional view that illustrates a configuration of an engagement unit of an operation input device according to a third embodiment of the present invention.
Figure 14B:
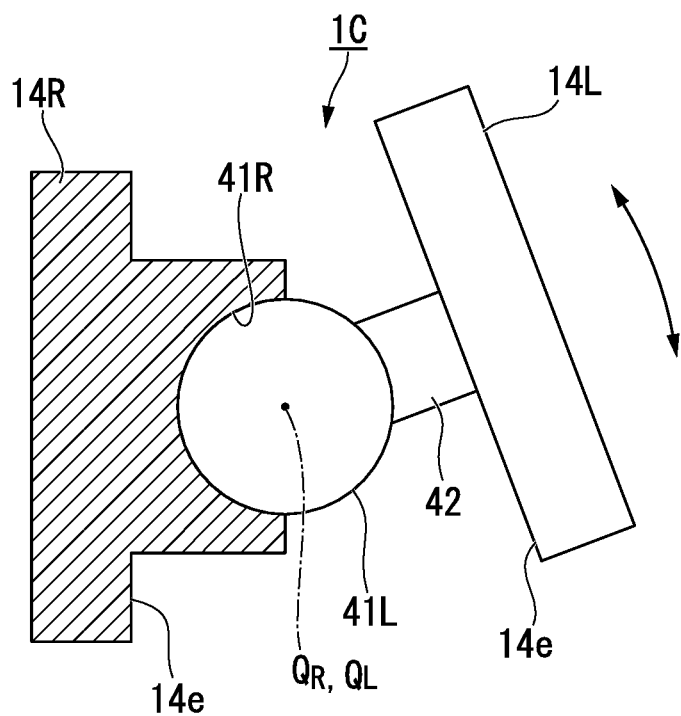
FIG. 14B is a partially schematic cross-sectional view that illustrates a configuration of an engagement unit of an operation input device according to the third embodiment of the present invention.

FIGS. 14A and 14B are schematic partial cross-sectional views that illustrate a configuration of an engagement unit of the operation input device according to the third embodiment of the present invention.

As main parts are shown in FIG. 14A, a master manipulator 1C (operation input device) according to the present embodiment includes engagement units 41R and 41L instead of the engagement units 19R and 19L of the master manipulator 1 according to the first embodiment mentioned above. Hereinafter, the points different from the first embodiment mentioned above will be mainly described.

The engagement unit 41R forms a semispherical concave portion in a distal end of a protrusion formed in the distal end surface 14e of the right hand operation arm 14R.

The engagement unit 41L forms a spherical body having the same diameter of the concave portion as the engagement unit 41R. The engagement unit 41L is included in the distal end of the support member 42 that is provided on the distal end surface 14e of the left hand operation arm 14L in a standing state.

For this reason, as shown in FIG. 14B, when inserting and engaging the engagement unit 41L to the engagement unit 41R, the engagement units are engaged with each other so as to be turnable about centers $Q_R$ and $Q_L$ in a state in which a center $Q_R$ of the concave portion of the engagement unit 41R coincides with a center $Q_L$ of a sphere of the engagement unit 41R.

In the present embodiment, the engagement is simple, and it is possible to easily maintain the engaged state in which the operator P holds the arms by hand. Furthermore, even when the operator P moves the right hand operation arm 14R and the left hand operation arm 14L of the engaged state, since tolerance of the orientation at the time of engagement is great, it is highly unlikely that the right hand operation arm 14R and the left hand operation arm 14L are disengaged at the time of movement. For this reason, in the present embodiment, the engagement sensor is omitted.

The method of initializing the master manipulator 1C according to the present embodiment can be performed in substantially the same manner as the initializing method according to the first embodiment mentioned above in accordance with the flow chart of FIG. 7.

However, the present embodiment is different in that the relative position is fixed so that the engagement units 41R and 41L can turn about one point coinciding with one point (center $Q_R$) on the right hand operation arm 14R and one point (center $Q_L$) on the left hand operation arm 14L at the time of engagement.

Hereinafter, the points different from the first embodiment mentioned above will be mainly described.

As shown in FIG. 14A, in the engagement process according to the present embodiment, the engagement units 41R and 41L are engaged with each other. The operator P holds the right hand operation arm 14R and the left hand operation arm 14L near the engagement units 41R and 41L so that the engagement unit 41L is not separated from the engagement unit 41R.

Furthermore, in the present embodiment, since the engagement sensor is not provided, a suitable input device is provided in the master control unit 100, and the operator P notifies the engagement detection unit 102 which finishes the engagement in step S2.

The data acquisition process can be performed in the same manner as the first embodiment mentioned above.

In the present embodiment, because there is a degree of freedom of the orientation change of the right hand operation arm 14R and the left hand operation arm 14L in the engaged state, the joint movement amount can be changed by suitably adding the turn about the centers $Q_R$ and $Q_L$.

In the initial value calculation process, since only the relative positions of the centers $Q_R$ and $Q_L$ are fixed, a condition that only the position coordinates $(X_R, Y_R, Z_R)$, $(X_L, Y_L, Z_L)$ coincide with each other is adopted. Thus, the present embodiment is different in that the equation number of equation (10) is a half that in the first embodiment mentioned above.

However, in the present embodiment, since the simultaneous equation is approximately solved by the iterative least squares technique, the calculation of the initial value is not particularly affected. For this reason, only the form of the specific simultaneous equation differs, and the initial value can be calculated by substantively the same convergent calculation.

In this manner, in the present embodiment, in substantially the same manner as the first embodiment mentioned above, it is possible to perform the initialization of the multi jointed arms 3R and 3L.

The present embodiment is an example of a case in which the engagement unit engages the distal ends of the multi jointed arms so as to be spherically rotatable about one point.

In addition, in the description of all the embodiments and modified examples, the cases that the two multi-jointed arms are provided are described, but the three or more multi-jointed arms may be provided.

In this case, the initialization may be performed so that the three or more respective distal ends are engaged with each other in one location to configure one closed link loop, and the initialization may be performed multiple times by combining the three or more multi jointed arms with two multi jointed arms.

Furthermore, in the description of all the embodiments and modified examples, the multi jointed arms of the same configuration are described as an example. However, this is an example, and the degree of freedom of the multi jointed arm, and the configuration of the combination of the specific joint with the arm is not limited thereto.

The embodiments and the modified examples of the present invention may adopt the multi-jointed arms of any configuration when the multi-jointed arms are connected in series by a plurality of joints performing the rotation motion or a translation motion and the position and the orientation of the distal end thereof to the proximal end thereof can be changed.

Furthermore, the configuration of the mutually engaged multi jointed arms may be suitably changed.

Herein, the expression "connected in series" means that the portions of the multi jointed arms performing the initialization are connected in series. Thus, a configuration including a branched arm that is not a target of the initialization is also within the scope of the present invention.

Furthermore, in the embodiments and the modified examples mentioned above, examples of cases in which the operator P maintains the engaged state of the engagement unit by hand are described. However, engagement fixing means for performing the fixing and the disengagement of the engaged state may be provided in the engagement unit or therearound.

As an example of the engagement fixing means, a mechanical fixing means such as a screw and a clamp, a magnetic fixing means using a magnet and so on, or the like can be adopted.

Furthermore, in the description of the embodiments and the modified examples mentioned above, an example of a case in which the engagement unit engages the distal ends of the multi jointed arms so that the relative position between the distal ends is fixed has been described. However, in the embodiments and the modified examples except for the third embodiment, the engagement units are configured to be fixed the distal end surfaces each other, as shown in FIG. 8B etc. At this time, since the distal end surfaces of the engagement units are mutually fixed, the distal ends of the engagement units are mutually fixed a relative orientation. Thus, the description of embodiments and the modified examples mentioned above is an example of a case in which the relative position and the relative orientation are fixed.

Furthermore, in the description of the second embodiment mentioned above, an example of a case in which initialization for the portions of the fifth joint 13 and the right hand operation arm 14R (left hand operation arm 14L) does not need to be performed due to the fact that the fifth joint 15 includes the detection unit $F_{13}$ in the multi jointed arms 3R (3L) has been described.

However, even in a case in which the fifth joint 13 includes the detection unit $E_{13}$ requiring the initialization, if the initialization not depending on the initializing method according to the present embodiment is performed, only the multi jointed arm units 30R (30L) may be initialized in the initializing method according to the embodiment of the present invention.

As the initializing method according to the embodiment of the present invention, for example, an initializing method of providing fixing means for fixing the mutual relative positional relationship to match the reference of the joint coordinate system between the L-shape arm 12 and the right hand operation arm 14R (left hand operation arm 14L), and transmits the reset signal to the detection unit $E_{13}$ in the engaged state may be used.

Furthermore, in the description of the first modified example mentioned above, an example of a case in which the detection target medium 22R and 22L are provided in the intermediate member 20 has been described. However, a configuration in which the detection target medium 22R and 22L of the intermediate member 20 and the engagement sensors 18R and 18L of the engagement units 19R and 19L are replaced may be adopted.

In this case, since there is no need to arrange the signal lines of the engagement sensors 18R and 18L in the multi-jointed arms 3R and 3L, the configuration of the multi jointed arms 3R and 3L can be simplified.

A configuration may be adopted which uses the engagement units 41L and 41R according to the third embodiment mentioned above instead of the respective engagement units between the right hand operation arm 14R, the intermediate member 20, and the left hand operation arm 14L according to the first modified example mentioned above. In this case, there is provided a configuration turnable engaged with the intermediate member 20 in a state in which the distance between two points on the right hand operation arm 14R and the left hand operation arm 14L is uniform.

Hereinabove, while preferred embodiments of the present invention have been described, the present invention is not limited to the embodiments. Additions, omissions, substitutions, and other modifications can be made to the present invention without departing from the spirit and scope of the present invention. The present invention is not limited to the above-mentioned description, and is only limited by the appended claims.

What is claimed is:

1. An operation input device that has two or more multi-jointed arms which have a plurality of joints in series having a degree of freedom of rotation or translation and are configured so that a position and an orientation of a distal end thereof relative to a proximal end thereof are changed, the operation input device comprising:
   a holding unit that holds the proximal ends of the multi-jointed arms in a state in which a relative positional relationship between the proximal ends is fixed;
   a detection unit that is provided in each of the plurality of joints to detect a joint movement amount that represents a movement of each of the plurality of joints by a rotation angle or a translational displacement from an unknown initial joint value;
   an engagement unit that is provided in each of the distal ends of the multi jointed arms and is engaged so that a relative position between the distal ends is fixed;
   a data acquisition unit that acquires a plurality of sets of joint movement amounts detected by the detection unit in a time series when engaging the distal ends of the multi jointed arms via the engagement unit and moving the mutually engaged distal ends; and
   an initial value calculation unit that calculates the unknown initial joint value under a condition that a relative positional relationship between the distal ends is fixed via the engagement unit based on the plurality of sets of joint movement amounts acquired by the data acquisition unit in a time series.

2. The operation input device according to claim 1, wherein the initial value calculation unit is configured to generate a simultaneous equation that sets the initial value of the joint movement amount as an unknown number based on a kinematical relational expression that describes positions and orientations of the distal ends of the multi-jointed arms, and the plurality of sets of joint movement amounts acquired by the data acquisition unit in a time series, and solve the simultaneous equation to calculate the initial value of the joint movement amount.

3. The operation input device according to claim 2, wherein the initial value calculation unit is configured to solve the simultaneous equation by performing a convergent calculation until a residual error expression to be zero in the simultaneous equation is less than or equal to a convergent determination value.

4. The operation input device according to claim 3, wherein the initial value calculation unit is configured to perform a warning when the convergent calculation is not finished within a predetermined time.

5. The operation input device according to claim 4, wherein the warning comprises warning of a breakdown of the detection unit.

6. The operation input device according to claim 1, wherein the engagement unit directly engages the distal ends of the multi jointed arms and fixes the relative position between the distal ends.

7. The operation input device according to claim 1, wherein the engagement unit engages the distal ends of the multi jointed arms so as to be spherically rotatable about one point.

8. The operation input device according to claim 1, wherein the engagement unit is engaged with an engagement unit of one of the multi jointed arms to be an engagement target via an intermediate member that constantly maintains a distance between the engagement unit and the engagement unit of the one of the multi jointed arms to be the engagement target.

9. The operation input device according to claim 1, wherein the engagement unit is engaged by fixing a relative position and a relative orientation between the distal ends of the multi jointed arms.

10. A method of initializing an operation input device that has two or more multi jointed arms which have a plurality of joints in series having a degree of freedom of rotation or translation and are configured so that a position and an orientation of a distal end thereof relative to a proximal end thereof are changed, and a detection unit which is provided in each of the plurality of joints to detect a joint movement amount that represents a movement of each of the plurality of joints by a rotation angle or a translational displacement from an unknown initial joint value, the method of initializing the operation input device comprising:
   a holding process of holding the proximal ends of the multi jointed arms in a state in which a relative positional relationship between the proximal ends is fixed;
   an engaging process of engaging the distal ends of the multi jointed arms so that a relative position between the distal ends is fixed;
   a data acquisition process of acquiring a plurality of sets of joint movement amounts in a time series from the detection unit that is provided in each of the plurality of joints of the mutually engaged multi jointed arms while moving the distal ends of the mutually engaged multi jointed arms; and an initial value calculation process of calculating the unknown initial joint value under a condition that a relative positional relationship between the distal ends is fixed by an engagement based on the plurality of sets of joint movement amounts acquired in the data acquisition process in a time series.

* * * * *